US011713961B2

(12) United States Patent
Tearney et al.

(10) Patent No.: US 11,713,961 B2
(45) Date of Patent: Aug. 1, 2023

(54) SYSTEMS, METHODS, AND MEDIA FOR MULTIPLE REFERENCE ARM SPECTRAL DOMAIN OPTICAL COHERENCE TOMOGRAPHY

(71) Applicant: THE GENERAL HOSPITAL CORPORATION, Boston, MA (US)

(72) Inventors: Guillermo J. Tearney, Cambridge, MA (US); Yogesh Verma, Medford, MA (US); David Odeke Otuya, Revere, MA (US); Romain Luu, Courbevoie (FR)

(73) Assignee: The General Hospital Corporation, Boston, MA (US)

( * ) Notice: Subject to any disclaimer, the term of this patent is extended or adjusted under 35 U.S.C. 154(b) by 20 days.

(21) Appl. No.: 17/473,308

(22) Filed: Sep. 13, 2021

(65) Prior Publication Data

US 2022/0170732 A1 Jun. 2, 2022

Related U.S. Application Data

(63) Continuation of application No. 16/755,478, filed as application No. PCT/US2018/055585 on Oct. 12, 2018, now Pat. No. 11,118,894.

(Continued)

(51) Int. Cl.
*G01B 9/02091* (2022.01)
*G01B 9/02015* (2022.01)
(Continued)

(52) U.S. Cl.
CPC ..... *G01B 9/02091* (2013.01); *G01B 9/02028* (2013.01); *G01B 9/02044* (2013.01);
(Continued)

(58) Field of Classification Search
CPC ............ G01B 9/02091; G01B 9/02028; G01B 9/02044; G01B 9/02049; G01B 9/02085;
(Continued)

(56) References Cited

U.S. PATENT DOCUMENTS

2006/0103850 A1   5/2006  Alphonse
2008/0002183 A1   1/2008  Yatagai
(Continued)

FOREIGN PATENT DOCUMENTS

JP        2013029317 A    2/2013
KR     20160117814 A   10/2016
(Continued)

OTHER PUBLICATIONS

Hyeon, M. G., et al. "Spectral domain optical coherence tomography with balanced detection using single line-scan camera and optical delay line." Optics express 23.18 (2015): 23079-23091.
(Continued)

*Primary Examiner* — Jonathan M Hansen
(74) *Attorney, Agent, or Firm* — Quarles & Brady LLP

(57) ABSTRACT

In some embodiments, systems, methods, and media for multiple reference arm spectral domain optical coherence tomography are provided which, in some embodiments, includes: a sample arm coupled to a light source; a first reference arm having a first path length; a second reference arm having a longer second path length; a first optical coupler that combines light from the sample arm and the first reference arm; a second coupler that combines light from the sample arm and the second reference arm; and an optical switch comprising: a first input port coupled to the first optical coupler; a second input coupled to the second coupler via an optical waveguide that induces a delay at least equal to an acquisition time of an image sensor; and an output coupled to the image sensor.

12 Claims, 10 Drawing Sheets

Related U.S. Application Data

(60) Provisional application No. 62/571,787, filed on Oct. 12, 2017.

(51) Int. Cl.
 *G01B 9/02* (2022.01)
 *A61B 5/00* (2006.01)
 *G01B 9/02055* (2022.01)

(52) U.S. Cl.
 CPC ..... *G01B 9/02049* (2013.01); *G01B 9/02085* (2013.01); *G01B 9/02087* (2013.01); *A61B 5/0066* (2013.01); *G01B 9/02078* (2013.01); *G01B 2290/35* (2013.01)

(58) Field of Classification Search
 CPC ............ G01B 9/02087; G01B 9/02078; G01B 2290/35; G01B 9/02064; A61B 5/0066
 See application file for complete search history.

(56) References Cited

U.S. PATENT DOCUMENTS

| | | |
|---|---|---|
| 2013/0301006 A1 | 11/2013 | Kim et al. |
| 2014/0125951 A1 | 5/2014 | Eom |
| 2015/0159992 A1* | 6/2015 | Buckland ........... G01B 9/02028 356/479 |
| 2015/0375336 A9 | 12/2015 | Webster |
| 2019/0206070 A1* | 7/2019 | Nash ................. G06T 7/33 |

FOREIGN PATENT DOCUMENTS

| | | |
|---|---|---|
| KR | 10-1706448 B1 | 2/2017 |
| WO | 2014100162 A1 | 6/2014 |

OTHER PUBLICATIONS

Jeong, H.-W., et al. "Spectral-domain OCT with dual illumination and interlaced detection for simultaneous anterior segment and retina imaging." Optics express 20.17 (2012): 19148-19159.

Otuya, D. O., et al. "Improved sensitivity roll-off in dual reference, buffered spectral-domain optical coherence tomography." Journal of Biomedical Optics 26.2 (2021): 025001.

Wu, T., et al. "Extending the effective imaging depth in spectral domain optical coherence tomography by dual spatial frequency encoding." Optical Coherence Tomography and Coherence Domain Optical Methods in Biomedicine XX. vol. 9697. International Society for Optics and Photonics, 2016.

European Patent Office. Extended European Search Report for application 18866648.1, dated Jun. 2, 2021. 10 pages.

International Searching Authority. International Search Report and Written Opinion for application PCT/US2018/055585, dated Feb. 1, 2019. 14 pages.

Ruggeri, M., et al. "Imaging and full-length biometry of the eye during accommodation using spectral domain OCT with an optical switch." Biomedical optics express 3.7 (2012): 1506-1520.

Wang, H. et al. "Extending the effective imaging range of Fourier-domain optical coherence tomography using a fiber optic switch." Optics letters 33.22 (2008): 2632-2634.

Japan Patent Office, Notice of Reasons for Refusal, Application No. 2020-520657, dated Aug. 2, 2022, 6 pages.

Japan Patent Office, Decision to Grant a Patent, Application No. 2020-520657, dated Feb. 7, 2023, 6 pages.

* cited by examiner

SYSTEMS, METHODS, AND MEDIA FOR MULTIPLE REFERENCE ARM SPECTRAL DOMAIN OPTICAL COHERENCE TOMOGRAPHY

CROSS REFERENCE TO RELATED APPLICATIONS

This application is a Continuation of U.S. application Ser. No. 16/755,478 filed on Apr. 10, 2020 which is a U.S. National Stage of PCT Application No. PCT/US2018/055585 filed on Oct. 12, 2018 which is based on, claims the benefit of, and claims priority to U.S. Provisional Application No. 62/571,787, filed Oct. 12, 2017, which are hereby incorporated herein by reference in their entirety for all purposes.

STATEMENT REGARDING FEDERALLY SPONSORED RESEARCH

N/A

BACKGROUND

Spectral domain optical coherence tomography (SD-OCT) is a type of optical coherence tomography that has become increasingly useful, as SD-OCT can generate data with relatively high sensitivity, high speed, and phase stability. However, conventional SD-OCT suffers from a depth-dependent sensitivity decay that decreases the utility of SD-OCT for imaging certain types of samples. For example, such depth-dependent sensitivity decay can decrease the usefulness of SD-OCT for imaging tissues with irregular surface topology and/or large luminal organs where the distance between the probe and the tissue surface often varies by a large amount.

In general, the sensitivity roll-off observed in SD-OCT systems is determined by the spectral resolution of the spectrometer used to capture the spectral domain image data. The spectral resolution of the spectrometer is, in turn, limited by the finite size and number of pixels in a linear detection array used to capture the image data.

Additionally, taking the Fourier transform of the real interference signal generated by an SD-OCT system leads to mirror images on both sides of the zero-delay. This makes it more difficult to readily distinguish between negative and positive image depths. To avoid this ambiguity, the zero delay is usually set at or outside the tissue surface, as the empty space between an SD-OCT probe and the surface generally does not generate much information. This makes it easier to generate images of the tissue, but also reduces the depth sensitivity as the empty space is sampled at high resolution, while tissue further from the surface is sampled at lower resolution, or not at all.

FIGS. 1A and 1B show examples 100 and 150 of conventional single reference arm spectral domain optical coherence tomography systems. FIG. 1A shows a representation of a widely used configuration of an SD-OCT system, which uses a Mach-Zehnder interferometer for SD-OCT. FIG. 1B is another widely used configuration of an SD-OCT system which uses a Michelson interferometer for SD-OCT. In these conventional SD-OCT systems, the imaging depth range is determined by both the number of pixels and width of the pixels in a linear detector used to acquire the spectrum. Generally, the number of pixels are sufficient to achieve relatively longer imaging depth range, but the finite width of the detector pixels limits the effective imaging depth range, as the width of the detector pixels determine the width of the spectrum acquired by each pixel. In general, the maximum imaging depth range is half the coherence length of the light acquired by each pixel. Additionally, due to conjugate symmetry, the zero-delay position is generally set outside of the sample to avoid the ambiguity between mirror images in the real signal. Accordingly, only half of the imaging range can generally be used for mirror artifact free images. Further, since the degree of coherence decays as a function of the path length difference, the sensitivity of an SD-OCT system rolls-off relatively rapidly and the measurement sensitivity is not sufficient to image the sample close to the edge of available imaging depth range.

As shown in FIG. 1A, a light source 102 can provide light to a sample arm and a reference arm via a polarization controller 104, an optical amplifier 106, and a fiber coupler 108. A portion of light is directed toward a sample arm (e.g., 80%), while a second portion of light is directed toward the reference arm (e.g., 20%). An optical circulator 110-1 directs light received from fiber coupler 108 toward a sample 112 (in the sample arm), and a second optical circulator 110-2 directs light toward a reference reflector 114 (in the reference arm). Light in the sample arm can be directed toward the sample via collimating optics 116-1 and focusing optics 118 (e.g., a lens), which can project a beam with a depth of focus centered near the surface of sample 112. A portion of the beam can be reflected at various depths of the sample as a function of reflectivity of the sample, which is then received by focusing optics 118 and directed toward optical circulator 110-1 via collimating optics 116-1, which directs the reflected light toward a fiber coupler 120 to be combined with light from the reference arm. Collimating optics 116-2 direct a beam from the reference arm toward reference reflector 114, which reflects the beam back toward optical circulator 110-2 via collimating optics 116-2, and optical circulator 110-2 directs the light reflected by reference reflector 114 toward fiber coupler 120 via a polarization controller 122 to be combined with light from the sample arm. Fiber coupler 120 combines the light from both the sample arm and the reference arm, and directs the light toward spectrometer 124, which generates a wavelength dependent signal representing the structure of the sample along the depth direction.

System 150 depicted in FIG. 1B operates using similar principles to system 100 depicted in FIG. 1A, but includes only a single optical circulator 110-3 before fiber coupler 108, rather than using an optical circulator in both the sample arm and reference arm. In both system 100 and system 150, the length of the reference arm can be set by adjusting the position of reference reflector 114 to set the depth of the zero-delay point with respect to sample 112.

Accordingly, new devices, systems, and methods for multiple reference arm spectral domain optical coherence tomography are desirable.

SUMMARY

In accordance with some embodiments of the disclosed subject matter, devices, systems, and methods for multiple reference arm spectral domain optical coherence tomography are provided.

In accordance with some embodiments of the disclosed subject matter, a system for spectral domain optical coherence tomography is provided, the system comprising: a light source; an image sensor; a sample arm coupled to the light source, wherein the sample arm is configured to cause light from the light source to be projected toward a sample; a first reference arm having a first path length, wherein the first reference arm is coupled to the light source and the sample arm; a second reference arm having a second path length that is longer than the first path length, wherein the second reference arm is coupled to the light source and the sample arm; a first optical coupler configured to combine light from the sample arm and light from the first reference arm; a second optical coupler configured to combine light from the sample arm and light from the second reference arm; and an optical switch comprising: a first port coupled to an output of the first optical coupler, a second port coupled to an output of the second optical coupler via a length of optical waveguide that induces a delay at least equal to an acquisition time of the image sensor, and a third port coupled to the image sensor, wherein the optical switch is configured to selectively provide light from one of the first port and the second port and block light from the other of the first port and the second port.

In some embodiments, the system further comprises: a processor that is programmed to: cause the optical switch to output light received by the first port during a first time window, cause the image sensor to generate a first vector of data based on light received during the first time window, wherein the first vector of data represents a state of the sample in the first time window that includes a first time, cause the optical switch to output light received by the second port during a second time window, cause the image sensor to generate a second vector of data based on light received during the second time window that includes a second time, wherein the second vector of data represents the state of the sample in the first time window, cause the optical switch to output light received by the first port during a third time window, wherein the third time window is subsequent to the first time window and second time window and includes neither the first time nor the second time, and cause the image sensor to generate a third vector of data based on light received during the third time window, wherein the third vector of data represents a state of the sample in the third time window.

In some embodiments, the first vector and the second vector correspond to a first lateral position on a surface of the sample, and wherein the third vector corresponds to a second lateral position on the surface of the sample.

In some embodiments, the processor is further programmed to generate a matrix of data, wherein the first vector is a first row of the matrix, the second vector is a second row of the matrix, and the third vector is a third row of the matrix.

In some embodiments, the first vector comprises at least N elements, wherein each of the N elements corresponds to a pixel of the image sensor, and wherein the matrix comprises at least N columns.

In some embodiments, a second optical path from the second optical coupler to the second port of the optical switch is longer than a first optical path from the first optical coupler to the first port of the optical switch by at least five light-microseconds.

In some embodiments, the second optical path from the second optical coupler to the second port of the optical switch is at least one kilometer long.

In some embodiments, the system further comprises a fiber splitter with an input coupled to the light source, a first output coupled to the sample arm, and a second output coupled to the first reference arm and the second reference arm, wherein the fiber splitter is configured to provide at least half of the light received at the input to the first output.

In some embodiments, the fiber splitter is configured to provide three quarters of the light received at the input to the first output.

In some embodiments, the fiber splitter is a first fiber splitter, and the system further comprises a second fiber splitter with an input coupled to the second output of the first fiber splitter, a first output coupled to the first reference arm, and a second output coupled to the second reference arm, wherein the second fiber splitter is configured to provide half of the light received at the input to the first output.

In some embodiments, the system further comprises: a first optical circulator coupled to the light source, the sample arm, the first optical coupler, and the second optical coupler; a second optical circulator coupled to the light source, the first reference arm, and the first optical coupler; and a third optical circulator coupled to the light source, the second reference arm, and the second optical coupler.

In some embodiments, the system further comprises a variable delay line coupled between the light source and the first reference arm.

In some embodiments, a sensitivity of the system is at least 98 dB over the entire imaging depth of the system.

In some embodiments, the second path length is longer than the first path length by half of the maximum imaging depth of the system.

In accordance with some embodiments of the disclosed subject matter, a method for spectral domain optical coherence tomography is provided, the method comprising: receiving, by a processor, a matrix of data comprising: a first vector of data generated using a first reference arm having a first path length and representing a state of a sample in a first time window that includes a first time, a second vector of data generated using a second reference arm having a second path length and representing the state of the sample in the first time window, a third vector of data generated using the first reference arm and representing a state of the sample in a second time window that does not include the first time, and a fourth vector of data generated using the second reference arm and representing the state of the sample in the second time window; generating, by the processor, first image data based on the first vector of data and the third vector of data; generating, by the processor, second image data based on the second vector of data and the fourth vector of data; calculating, by the processor, a spatial offset between the first image data and the second image data based on a comparison of a portion of the first image data and a portion of the second image data; appending, by the processor, a first plurality of vectors to the portion of the first image data to generate a zero padded image, wherein the number of vectors appended is based on the spatial offset; removing, by the processor, a second plurality of vectors from the second image data to generate a cropped image, wherein the number of vectors removed is based on the spatial offset; and merging, by the processor, the zero padded image and the cropped image to generate an image of the sample with decreased sensitivity roll-off.

In some embodiments, the first vector is a first row of the matrix and the second vector is a second row of the matrix.

In some embodiments, the first vector comprises at least N elements, each of the N elements corresponds to a pixel of the image sensor, and the matrix comprises at least N columns.

In some embodiments, the spatial offset corresponds to a particular number of columns of the N columns.

In some embodiments, each entry in the first vector corresponds to a wavelength, and wherein the method further comprises mapping the wavelength for each element to a wavenumber k.

In some embodiments, the method further comprises performing a discrete Fourier transform to convert each element of the first vector to a depth value.

In some embodiments, further comprising generating a real image of the sample based on the first image data by subdividing the matrix into two submatrices by selecting vectors on a positive side of a zero delay for inclusion in a first submatrix and selecting vectors on a negative side of the zero delay for inclusion in a second submatrix.

In some embodiments, the portion of the first image data corresponds to the first submatrix.

In some embodiments, further comprising generating a binary mask based on the second submatrix.

In some embodiments, further comprising generating a weighting matrix W comprising a plurality of weighting coefficients Cm based on the binary mask and a function.

In some embodiments, the function is $C_m=(\tanh(x)+1)/2$, where x varies from $-2\pi$ to $2\pi$.

In some embodiments, the first vector and the second vector correspond to a first lateral position on a surface of the sample, and the third vector and fourth vector correspond to a second lateral position on the surface of the sample.

In accordance with some embodiments of the disclosed subject matter, a non-transitory computer readable medium containing computer executable instructions that, when executed by a processor, cause the processor to perform a method for spectral domain optical coherence tomography is provided, the method comprising: receiving, by a processor, a matrix of data comprising: a first vector of data generated using a first reference arm having a first path length and representing a state of a sample in a first time window that includes a first time, a second vector of data generated using a second reference arm having a second path length and representing the state of the sample in the first time window, a third vector of data generated using the first reference arm and representing a state of the sample in a second time window that does not include the first time, and a fourth vector of data generated using the second reference arm and representing the state of the sample in the second time window; generating, by the processor, first image data based on the first vector of data and the third vector of data; generating, by the processor, second image data based on the second vector of data and the fourth vector of data; calculating, by the processor, a spatial offset between the first image data and the second image data based on a comparison of a portion of the first image data and a portion of the second image data; appending, by the processor, a first plurality of vectors to the portion of the first image data to generate a zero padded image, wherein the number of vectors appended is based on the spatial offset; removing, by the processor, a second plurality of vectors from the second image data to generate a cropped image, wherein the number of vectors removed is based on the spatial offset; and merging, by the processor, the zero padded image and the cropped image to generate an image of the sample with decreased sensitivity roll-off.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1A:
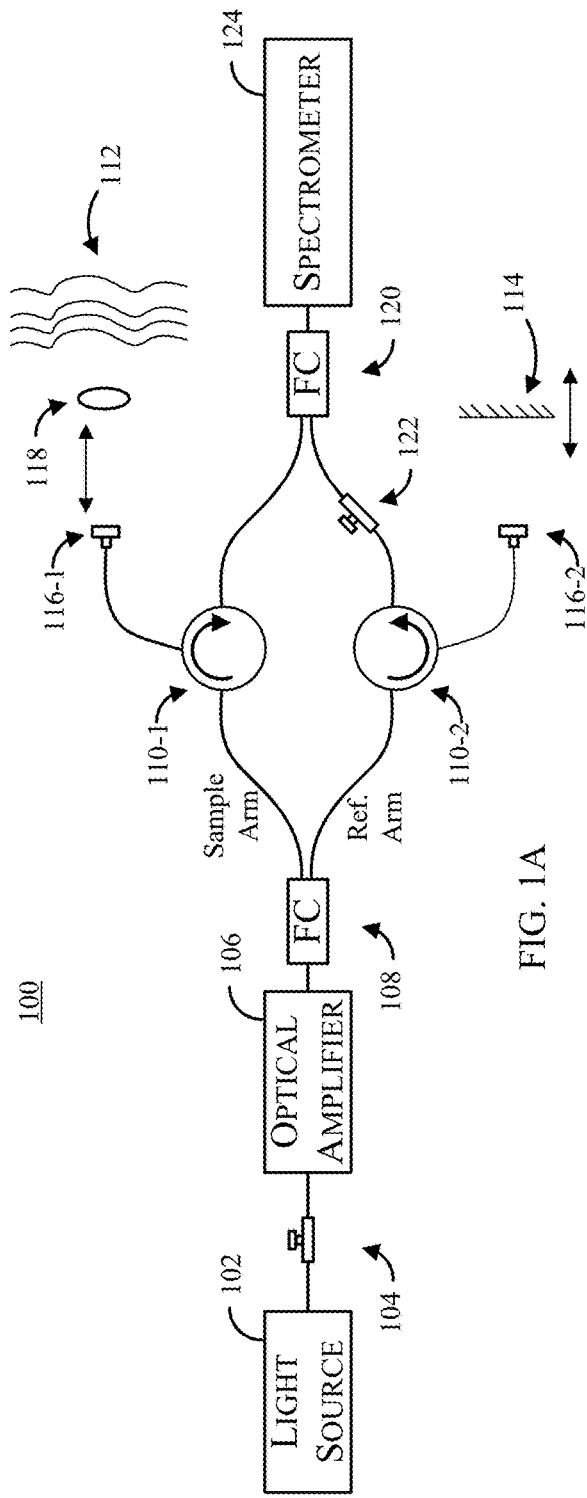
FIG. 1A shows an example of a conventional single reference arm spectral domain optical coherence tomography system.
Figure 1B:
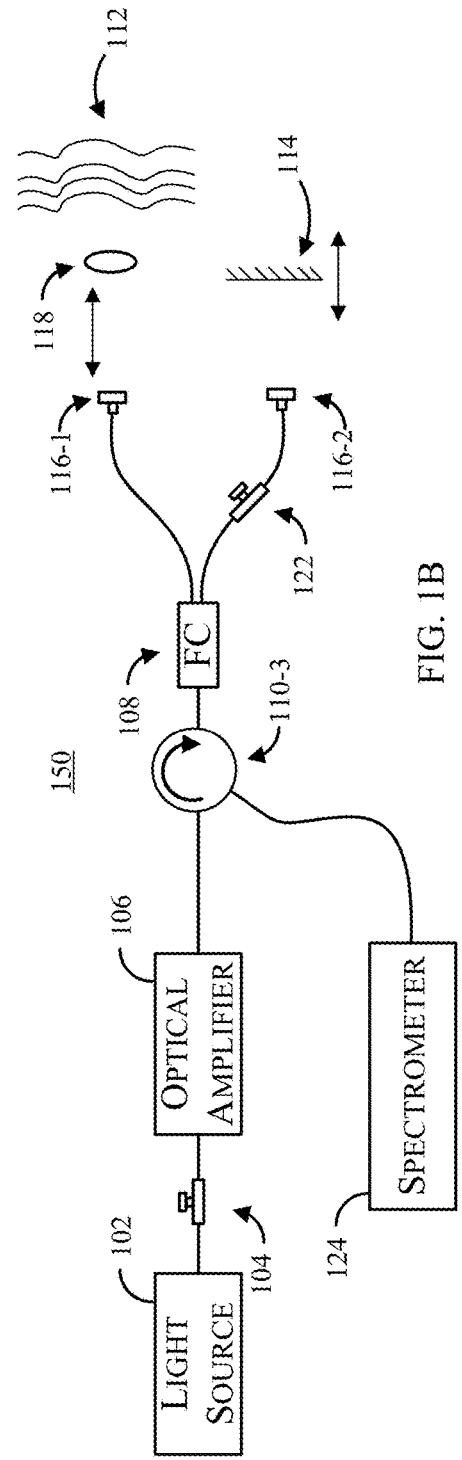
FIG. 1B shows another example of a conventional single reference arm spectral domain optical coherence tomography system.

In accordance with some embodiments of the disclosed subject matter, mechanisms (which can include devices, systems, and methods) for multiple reference arm spectral domain optical coherence tomography are provided.

In accordance with some embodiments of the disclosed subject matter, the mechanisms described herein can be used to implement an SD-OCT system with reduced sensitivity roll-off (e.g., compared to conventional SD-OCT systems) using multiple reference arm delays. In some embodiments, the optical delay between multiple reference arms can be adjusted such that the most sensitive region for respective images generated using the multiple reference arms are set near the surface of a sample for a first reference arm, and within the sample at about half the ranging depth of the first reference arm. In some embodiments, the mechanisms described herein can use a fiber delay line to delay interferograms from one reference arm temporally such that interference originating from the same sample location in the same temporal window can be detected by a single detector. In some embodiments, the mechanisms described herein can combine images obtained from multiple reference arm delays, producing a resultant image that has reduced sensitivity roll-off and extended imaging depth range.

As described below, an SD-OCT system implemented using mechanisms described herein had a maximum sensitivity of >105 dB and a minimum sensitivity of 95 dB over a 6-mm ranging depth, and images of tissue acquired ex vivo demonstrates the capability of such a system to more clearly visualize tissue at the edges of the ranging depth range.

In some embodiments, electromagnetic radiation reflected from a sample can be split and combined with different reference beams having different path lengths. For example, the electromagnetic radiation in one reference arm can be delayed by half of the imaging range of the system with respect to the other reference arm, and can be combined with half of the electromagnetic radiation reflected from the sample to generate an interference pattern. As another example, the electromagnetic radiation from the second reference arm can be combined with the other half of the electromagnetic radiation reflected from the second to generate a separate interference pattern representing a different portion of the sample. In such examples, the two interference patterns can correspond to the back-scattered electromagnetic radiation from the sample interfered with reference electromagnetic radiation with two different path lengths.

In some embodiments, the path length (sometimes referred to herein as the delay) of one or more reference arms can be adjusted using an optical circulator that directs light from a light source toward a reference mirror, with the position of the reference mirror being adjustable. Additionally or alternatively, one or more reference arms can omit a reference mirror, and the reference beam can be provided by passing light from the light source through optics with a path length that is about the same as the path length to the sample and back to the reference arm. For example, light from a light source can be split toward two reference arms, with the reference arm light from a reference arm of fixed path length being directed to a fiber coupler (e.g., a 99/1 fiber coupler), while another reference arm can be configured to have a variable path length that can be adjusted (e.g., by stretching the fiber, by increasing the length in free space, etc.).

In some embodiments, after combining electromagnetic radiation reflected from the sample with electromagnetic radiation from the reference arms, and before passing the electromagnetic radiation corresponding to the interference patterns created by the combination of sample arm electromagnetic radiation and reference arm electromagnetic radiation to an interferometer (e.g., via an optical switch), the combined electromagnetic radiation corresponding to one (or more) of the reference arms can be delayed by passing the electromagnetic radiation through a length of fiber optic waveguide (e.g., a single mode optical fiber) to temporally delay the electromagnetic radiation with respect to the combined electromagnetic radiation corresponding to another reference arm. For example, the length of the optical fiber can be configured to temporally delay the electromagnetic radiation from a particular reference arm by an amount of time taken to acquire information from the electromagnetic radiation of the other reference arm by a linear detector.

In some embodiments, the spectrum of the interfered electromagnetic radiation from each reference arm can be detected by dispersing the interfered electromagnetic radiation as a function of wavelength in one dimension toward a detector array. For example, the dispersed signal can be detected by a spectrometer or a line scan camera. Note that although linear arrays of CCD pixels are generally described herein as being used to detect such electromagnetic radiation, this is merely an example, and in some cases a portion of a two dimensional array can be used to detect such electromagnetic radiation.

In some embodiments, an optical switch can be used to alternately pass the interfered electromagnetic radiation from each reference arm sequentially in order to alternately detect multiple interfered electromagnetic signals that represent a sample in a particular time window. In some embodiments, the sequential detection of the spectra of the multiple interfered electromagnetic radiation corresponding to the multiple reference arms can ensure that acquired interference spectra correspond to the same time window, as the electromagnetic radiation from one reference arm is temporally delayed by the same duration that is used to detect each single spectrum.

In some embodiments, sequentially acquired spectra can be processed to combine the information representing interference with light from each reference arm. For example, the spectra can be processed by subtracting the background, performing a fast Fourier transformation to generate depth information (e.g., representing a reflectivity profile of sample in the axial/depth direction). In such an example, resultant depth information can be used to generate image data using the depth information corresponding to both of the reference arms. In some embodiments, using the mechanisms described herein can be used to produce a resultant image that has reduced sensitivity roll-off and extended imaging depth range (e.g., compared to conventional SD-OCT systems), which can mitigate one of the largest disadvantages of conventional SD-OCT systems.

Various other schemes have been explored for mitigating the sensitivity roll-off of SD-OCT. For example, one scheme uses reference arm or sample arm phase shifting to introduce a carrier frequency to facilitate quadrature detection. The complex spectral interference signal from the quadrature detector allows the positive and negative delay signals to be more easily distinguished, which facilitates placing the zero-delay in the middle of the ranging depth, increasing the depth from which high resolution signals can be detected with higher sensitivity. However, such quadrature detection approaches typically require multiple additional optical components that induce losses, which decreases the overall maximum OCT sensitivity that can be achieved.

As another example, one scheme uses an optical switch in an interferometer's reference arm to alternate the transmission of two different reference arm delays. In such an example, a single reference arm can include multiple reflectors at different path lengths, and the light in the reference arm can be alternately passed along each path. Interference spectra corresponding to each reference delay are sequentially acquired using a single spectrometer, and then combined by concatenating the highest sensitivity portions of cropped images generated from each reference arm. While this approach can increase sensitivity at depth, because the images are acquired at different points in time, transverse resolution can be expected to be reduced for images obtained with high-speed scanning SD-OCT systems.

As yet another example, one scheme uses dual reference arms with corresponding, separate interferometers with separate light sources and line scan cameras used to capture information from each reference arm. This scheme introduces additional complications (e.g., through the introduction of different light sources, different sensors, etc.), and is also bulkier and more costly than schemes that use only a single spectrometer.

As still another example, another scheme multiplexes multiple sequentially acquired spectra with slightly offset frequency combs to attempt to reduce sensitivity roll-off. While this approach can reduce sensitivity roll-off, transverse resolution can be expected to be reduced for images obtained with SD-OCT systems due to the sequential acquisition of data.

Figure 2A:
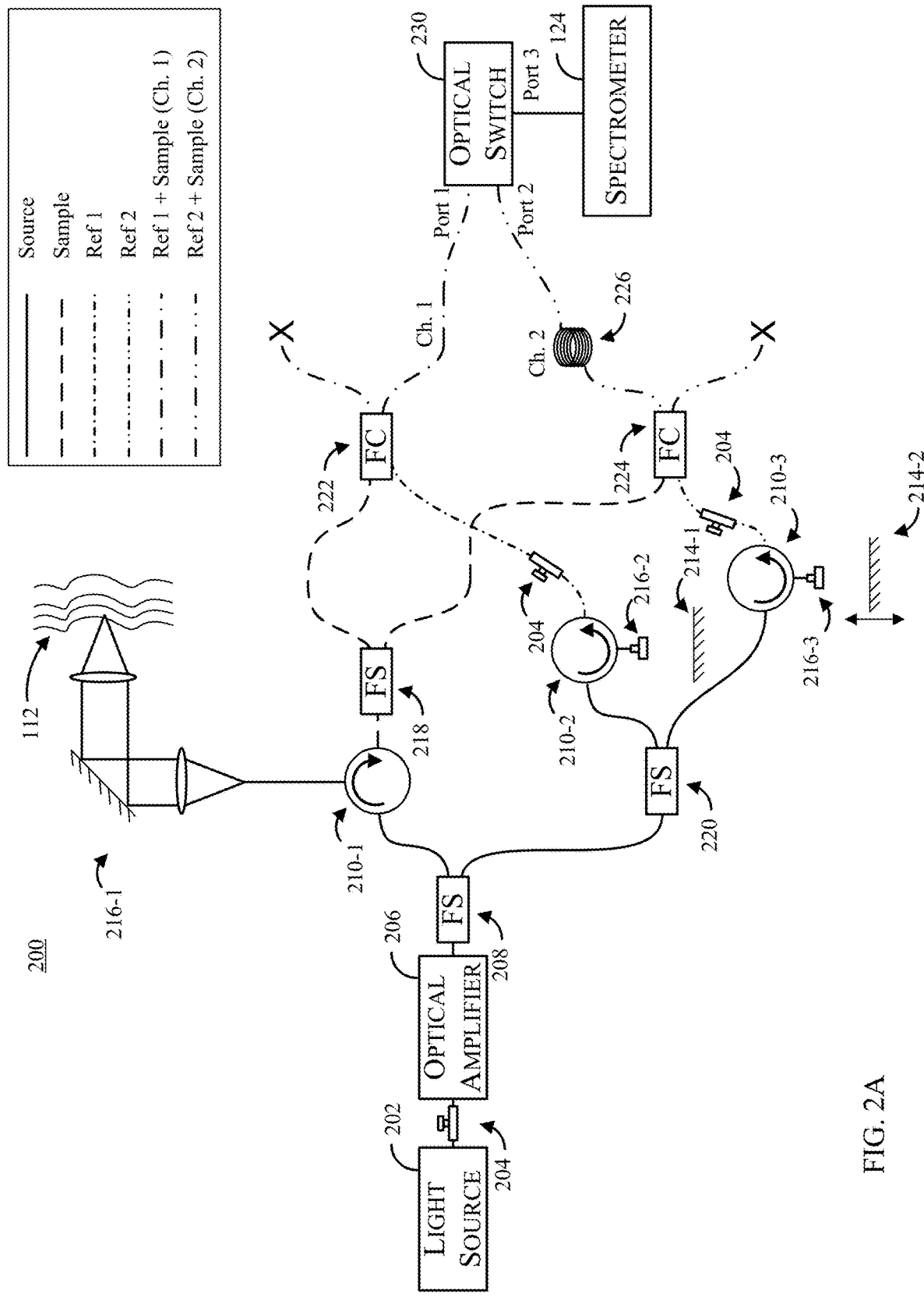
FIG. 2A shows an example of a system for multiple reference arm spectral domain optical coherence tomography in accordance with some embodiments of the disclosed subject matter.

FIG. 2A shows an example 200 of a system for multiple reference arm spectral domain optical coherence tomography in accordance with some embodiments of the disclosed subject matter. In some embodiments, system 200 can include an electromagnetic source 202 (referred to herein as light source 202 for convenience). Light source 202 can be any suitable light source or light sources. For example, light source 202 can be implemented using a superluminescent diode.

In some embodiments, light source 202 can emit electromagnetic radiation (referred to herein as "light" for convenience) to an optical amplifier 206. Additionally, in some embodiments, a polarization controller 204 can alter the polarization state of light emitted toward optical amplifier 206, which can be used to affect the gain of optical amplifier 206.

In some embodiments, light from light source 202 can be received by a fiber splitter 208, which can be used to split the input light into two outputs, a first output that can be directed toward a sample arm, and a second output that can be directed toward multiple reference arms. Fiber splitter 208 can split the input light into any suitable portions. For example, fiber splitter 208 can be a 75/25 fiber splitter that directs 75% of the input light toward the sample arm, and directs 25% of the input light toward the reference arms.

In some embodiments, an optical circulator 210-1 can receive light output from one port of fiber splitter 208, and can direct the light to a sample arm of system 200. In some embodiments, the sample arm can include optics 216-1 that can be used to direct a beam of light toward sample 112. In some embodiments, optics 216-1 can include any suitable optics for generating a beam with a sufficient depth of focus to generate data that can be used to generate optical coherence tomography signals. In some embodiments, optics 216-1 can be configured to direct light toward a particular location. For example, optics 216-1 can include one or more components that can be actuated to change a direction of an output beam.

In some embodiments, a portion of the light directed toward sample 112 light is reflected from sample 112 and received by optics 216-1, which directs the reflected light back toward optical circulator 210-1. Optical circulator 210-1 can direct light received from optics 216-1 toward another fiber splitter 218. In some embodiments, fiber splitter 218 can split the input light, and direct portions of the reflected light toward fiber couplers that can be used to combine the light reflected from the sample with light from each reference arm. Fiber splitter 218 can split the input light into any suitable portions. For example, fiber splitter 218 can be a 50/50 fiber splitter (e.g., a 1×2 or 2×2 3 dB fiber splitter) that directs 50% of the input light toward a first fiber coupler associated with a first reference arm, and directs 50% of the input light toward a second fiber coupler associated with a second reference arm.

In some embodiments, the portion of light directed toward the reference arms by fiber splitter 208 can be received by another fiber splitter 220, which can split the light again to direct a portion of light from the light source toward each reference arm. Fiber splitter 220 can split the input light into any suitable portions. For example, fiber splitter 220 can be a 50/50 fiber splitter (e.g., a 1×2 or 2×2 3 dB fiber splitter) that directs 50% of the input light toward a first reference arm, and directs 50% of the input light toward a second reference arm.

In some embodiments, each output of fiber splitter 220 can be coupled to an optical circulator. For example, a first reference arm can include an optical circulator 210-2, and a second reference arm can include an optical circulator 210-3.

In some embodiments, each optical circulator (e.g., 210-2 and 210-3) can direct the light toward a reference reflector 214-1 and 214-2, respectively (e.g., via optics 216-2 and 216-3, respectively). Each optical circulator 210-2 and 210-3 can receive the light reflected by the corresponding reference reflector 214-1 and 214-2, and can direct the reflected light toward a corresponding fiber coupler. For example, in some embodiments, optical circulator 210-2 can direct light reflected by reference reflector 214-1 toward a first fiber coupler 222 that is also configured to receive a portion of light reflected by sample 112 (e.g., from fiber splitter 218). As another example, in some embodiments, optical circulator 210-3 can direct light reflected by reference reflector 214-2 toward a second fiber coupler 224 that is also configured to receive a portion of light reflected by sample 112 (e.g., from fiber splitter 218). As shown in FIG. 2A, in some embodiments, a polarization controller 204 can be disposed between an optical circulator in a reference arm to control the polarization of light directed toward the corresponding fiber couplers. In some embodiments, fiber couplers 222 and 224 can be implemented using any suitable fiber coupler. For example, fiber coupler 222 (and/or fiber coupler 224) can be a 99/1 fiber coupler that is configured to combine about half of the light reflected from sample 112 with light reflected from reference reflector 214-1 (or from reference reflector 214-2).

In some embodiments, the optical path length of one or more of the reference arms can be controlled by positioning reference reflectors 214-1 and/or 214-2 using any suitable technique. For example, in some embodiments, reference reflectors 214-1 and/or 214-2 can be associated with an actuator that can controllably position the reference reflector. In a more particular example, one of the reference reflectors (e.g., reference reflector 214-1) can be positioned to provide a path length corresponding to the path length along the sample arm to a surface of sample 112, while another reference reflector (e.g., reference reflector 214-2) can be positioned to provide a path length corresponding to the path length along the sample arm to a point within sample 112 (e.g., longer than half the maximum imaging depth range that can be realized using the other reference reflector).

In some embodiments, the combined light from each fiber coupler 222 and 224 can be directed toward a separate port of an optical switch 230. In some embodiments, a path from fiber coupler 222 to a first port of optical switch 230 can be a first length, while a path from fiber coupler 224 to a second port of optical switch 230 can be a second length. For example, as shown in FIG. 2A, the path from fiber coupler 224 can include a length of single mode optic waveguide 226 that can delay the arrival of light from fiber coupler 224 to optical switch 230.

In some embodiments, a length of optic waveguide 226 can be configured to delay light from fiber coupler 224 by an amount of time that a sensor of a spectrometer 124 uses to collect a single line of data. In such embodiments, system 200 can control optical switch 230 to alternately provide light from fiber coupler 222 and fiber coupler 224 to spectrometer 124 at a frequency based on the amount of time taken to collect a single line of data. Due to the delay provided by optic waveguide 226, the light provided from fiber coupler 224 can represent the state of the sample at substantially the same time that as that represented by light provided from fiber coupler 222. Accordingly, the light received sequentially by spectrometer 124 from fiber couplers 222 and 224 can substantially correspond to the state of sample 112 during the same time window, which can facilitate imaging with greater depth penetration, while rendering the imaging insensitive to motion of the sample that may otherwise cause artifacts in sequentially acquired images. Note that the output of fiber coupler 222 is sometimes referred to herein as channel 1, while the output of fiber coupler 224 is sometimes referred to herein as channel 2.

In some embodiments, an image sensor of spectrometer 124 can be operated in a line trigger mode that causes a line of data to be acquired on each rising edge of a trigger signal (e.g., a TTL signal), or alternatively, on each falling edge of a trigger signal. In such embodiments, another signal can be used to control optical switch 230 such that data is alternately acquired from channel 1 and channel 2. For example, the signal that controls optical switch 230 can have a frequency that is synchronous with the trigger signal, but has a lower frequency by half. In such an example, the optical switch control signal can rise or fall in a synchronous fashion with the trigger signal such that the optical switch control signal transitions at the same time that the trigger signal transitions. This synchronous operation can ensure the sequential acquisition of data from channel 1 and channel 2 captures information that corresponds in time.

Figure 2B:
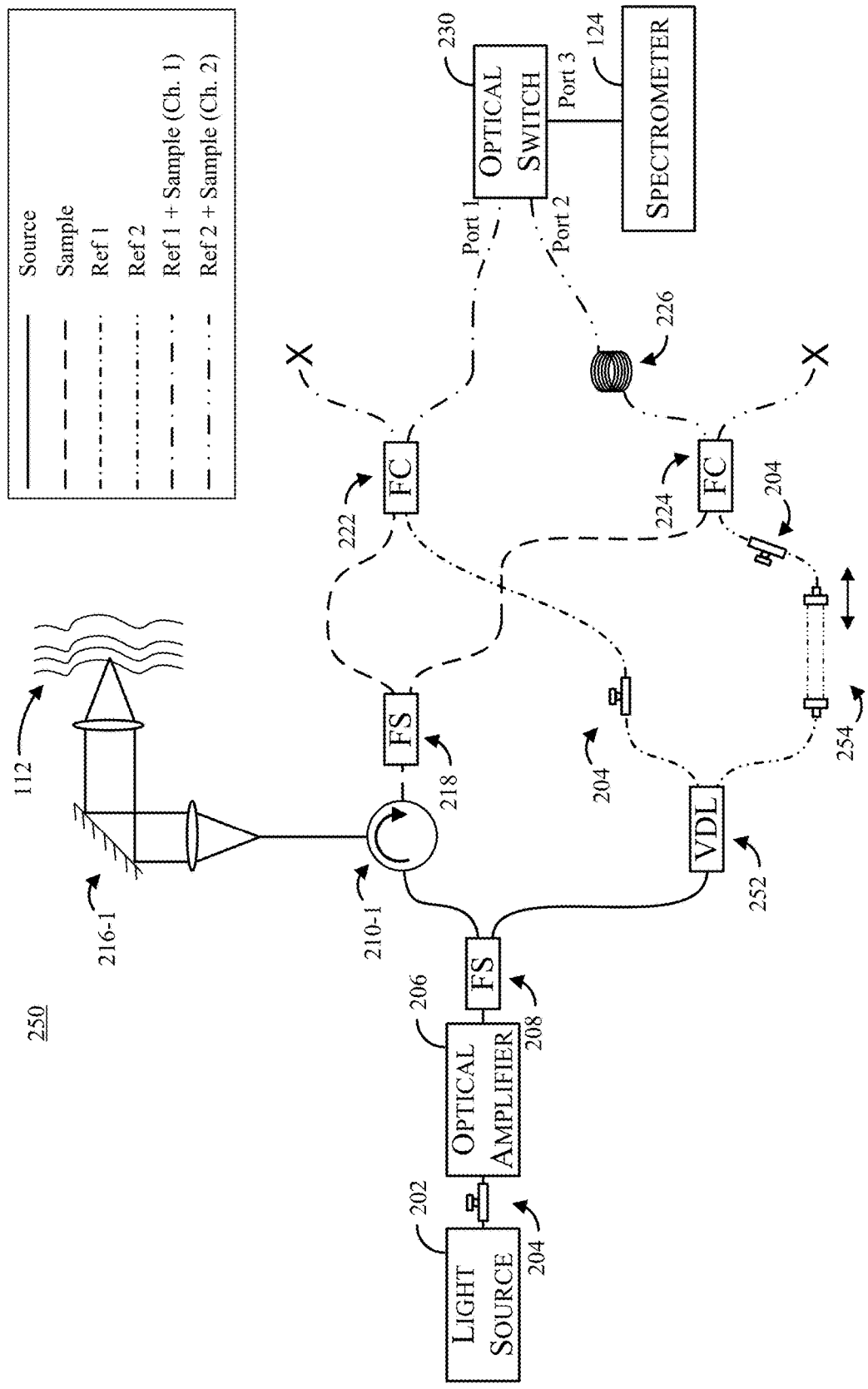
FIG. 2B shows another example of a system for multiple reference arm spectral domain optical coherence tomography in accordance with some embodiments of the disclosed subject matter.

FIG. 2B shows another example 250 of a system for multiple reference arm spectral domain optical coherence tomography in accordance with some embodiments of the disclosed subject matter. As shown in FIG. 2B, system 250 can include reference arms that are implemented using a variable delay line 252 in lieu of reference reflectors to create a path length that substantially corresponds to the path length to sample 112 along the sample arm. In such embodiments, several optical components can be eliminated, such as optical circulators 210-2 and 210-3 can be eliminated, optics 216-2 and 216-3, and reference reflectors 214-1 and 214-2. In some embodiments, a variable component 254 can be included in one of the reference arms to facilitate control of the path length of the reference arm. For example, variable component 254 can be an air gap with an adjustable length, a stretchable portion of fiber with an adjustable length, etc.

Figure 3:
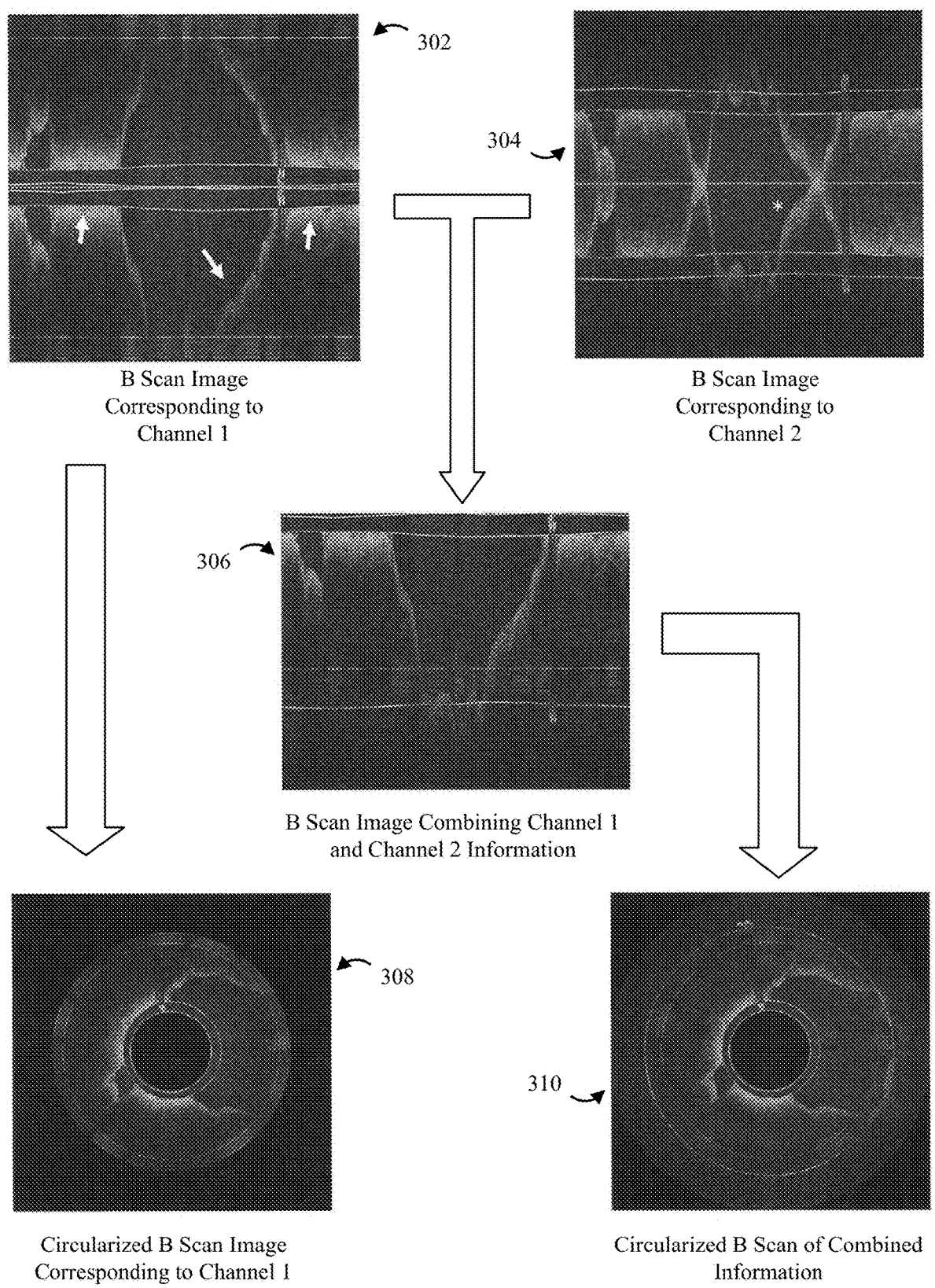
FIG. 3 shows examples of images generated using multiple reference arms of a multiple reference arm spectral domain optical coherence tomography system implemented in accordance with some embodiments of the disclosed subject matter.

FIG. 3 shows examples of images generated using multiple reference arms of a multiple reference arm spectral domain optical coherence tomography system implemented in accordance with some embodiments of the disclosed subject matter. As described in more detail below, an acquired two-dimensional data matrix can include data from both channel 1 and channel 2 in alternate columns (or rows), and OCT images can be generated from the acquired data matrix by de-interleaving the data from each channel, removing a background component from each channel, remapping wavelength data to wavenumber data, performing a fast Fourier transformation on the wavenumber data, and mixing of the images generated form each channel. For example, odd lines of the data matrix can include spectra from channel 1, while even lines of the data matrix include spectra from channel 2 which is delayed with an offset (e.g., of about 3 millimeters (mm)). In such an example, the odd and even lines of the data matrix can be separated to produce separate images corresponding to channel 1 and channel 2, which can be processed separately. In some embodiments, the mean of all spectra (e.g., in each channel) can be subtracted from each spectrum of the corresponding data set for background removal. For example, spectra from channel 1 can be averaged, and the average value can be subtracted from each value in the data matrix corresponding to channel 1. Note that the mean can be generated using the combined data, but the losses in the two channels may be different, causing a difference in the background value.

In some embodiments, after background removal, each spectrum can be remapped from a linear wavelength domain to a linear wavenumber domain using a mapping function calibrated for the spectrometer. In some embodiments, the re-mapped spectra can be fast Fourier transformed to generate a reflectivity profile in the depth domain.

As shown in FIG. 3, image 302 is a cross-sectional OCT image of a sample corresponding to channel 1, while image 304 is a cross-sectional OCT image of the sample corresponding to channel 2. As described above, due to the longer path length of the reference arm corresponding to channel 2, image 304 represents a portion of the sample that is deeper within the tissue than the portion represented in image 302 (although there is substantial overlap). Additionally, the delay in channel 2 after the light reflected from the sample is combined with the light reflected from the reference reflector can cause the data in image 304 to represent substantially the same time windows that are represented in image 302.

In general, SD-OCT systems have larger sensitivity roll-off than swept source OCT (SS-OCT) systems, signal strength rapidly decays with optical delay in SD-OCT systems. This relatively rapid signal strength decay can be observed in images 302 and 304. For example, in image 302 the signal strength for tissue surface closer to an imaging probe surface (shown by solid arrows pointing "up") is stronger than that of tissue surface at longer distance from the probe surface (shown by the solid arrow pointing more "down"). However, in image 304, which has an additional optical delay offset, the tissue surface located at longer distance from the image probe surface (shown by a solid asterisk) is relatively stronger than that same point in image 302. Note that the zero-optical delay was set just before the inner surface of the image probe wall when capturing data used to generate image 302, which causes a separation in the mirror images caused by the ambiguity between positive and negative delays in SD-OCT data. Conversely, the zero-optical delay was set within the imaging probe surface when capturing data used to generate image 304, and the mirror images consequently overlap in image 304. Accordingly, in some embodiments, information from image 302 can be used to remove mirror image artifacts from image 304 prior to merging of the images to generate image 306. Image 308 is a version of image 302 in Cartesian coordinates, and image 310 is a version of image 306 in Cartesian coordinates. As shown in FIG. 3, image 310 includes more information at greater depths.

Figure 4:
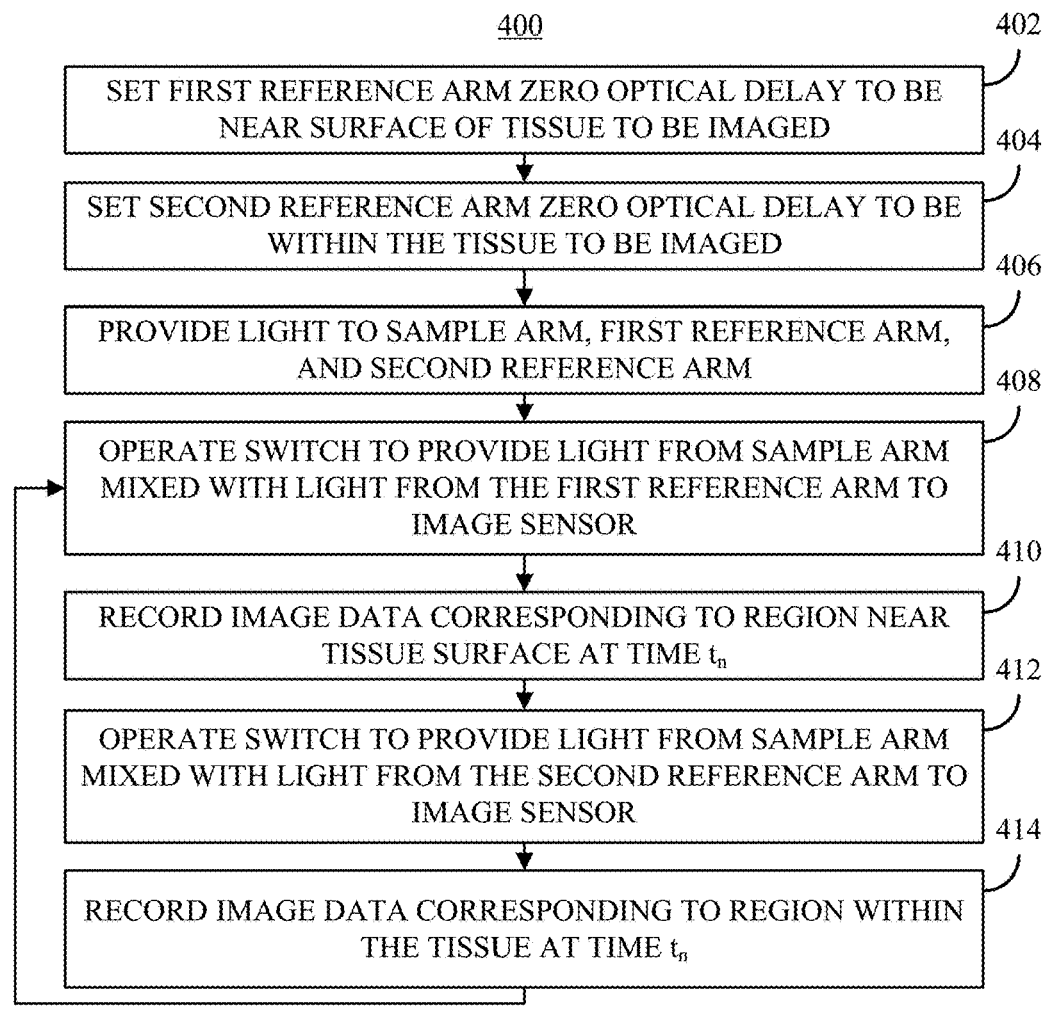
FIG. 4 shows an example of a process for generating spectral domain optical coherence tomography image data using multiple reference arms in accordance with some embodiments of the disclosed subject matter.

FIG. 4 shows an example 400 of a process for generating spectral domain optical coherence tomography image data using multiple reference arms in accordance with some embodiments of the disclosed subject matter. As shown in FIG. 4, at 402, process 400 can include setting a first reference arm zero optical delay to be near a surface of a sample (e.g., an in-vivo tissue sample) to be imaged. For example, the zero optical delay can be set to be just outside the surface of the sample to prevent formation of mirror artifacts in an OCT image generated using the first reference arm. In some embodiments, the path length of the first reference arm can be set using any suitable technique or combination of techniques. For example, in some embodiments, the path length of the first reference arm can be fixed based on an expected distance between a probe (e.g., including optics 216-1) and the tissue surface. As another example, the path length of the first reference arm can be manually adjusted. In a more particular example, the path length can be set at an initial value, and an operator can adjust the path length until a relatively small separation between mirror images is observed between the positive and negative delay images generated based on the first reference arm. As yet another example, the path length of the first reference arm can be automatically adjusted to a value just before the surface of the sample using any suitable technique or combination of techniques, such as an active or passive range finding operation, analysis of data acquired using the first reference arm, etc.

At 404, process 400 can include setting a second reference arm zero optical delay to be within the sample to be imaged. For example, the zero optical delay can be set to be about half the maximum imaging depth that can be achieved using the first reference arm. As the first reference arm can be expected to have a zero optical delay at the tissues surface, data is generally only collected up to half of the maximum imaging depth that could be achieved if the zero optical delay were set within the tissue (although this would result in an image with overlapping mirror images). In some embodiments, the path length of the second reference arm can be set using any suitable technique or combination of techniques. For example, in some embodiments, the path length of the second reference arm can be fixed based on an expected imaging depth of the first reference arm (e.g., the path length can be fixed at about 3 mm longer than the path length of the first reference arm). As another example, the path length of the second reference arm can be manually adjusted. In a more particular example, the path length can be set at an initial value, and an operator can adjust the path length until a merged image (and/or an image produced using only information generated using the second reference arm) includes data from depths of the tissue that overlap a sufficient amount with the first reference arm, while also including data from depths substantially beyond the maximum imaging depth of the first reference arm. As yet another example, the path length of the second reference arm can be automatically adjusted to provide a maximum imaging depth.

At 406, process 400 can provide light to a sample arm, the first reference arm, and a second reference arm. For example, as described above in connection with FIG. 2A, light can be provided to the sample arm via a first fiber splitter (e.g., fiber splitter 208), while the light can be provided to the first reference arm and second reference arm via two fiber splitters (e.g., fiber splitter 208 and fiber splitter 220).

At 408, process 400 can operate an optical switch to provide light reflected from the sample arm mixed with light reflected by the first reference arm.

At 410, process 400 can record image data corresponding to a region near a surface of the sample at a time $t_n$ based on the light received from the optical switch at 408. For example, as described above in connection with FIG. 2A, at 410, process 400 can control an image sensor (e.g., a linear CCD or linear CMOS sensor) to capture data indicative of depths at which light was reflected by the sample based on interference between light in the sample arm and light in the first reference arm.

At 412, process 400 can operate the optical switch to provide light reflected from the sample arm mixed with light reflected by the second reference arm. In some embodiments, process 400 can control the optical switch to account for the time used to acquire the image data from the first channel, and the delay in the second channel. For example, as described below in connection with FIG. 5, the image sensor can be operated using a trigger signal with a frequency having a period that is substantially the same as the time the linear sensor uses to acquire a single line of data.

At 414, process 400 can record image data corresponding to a region within the sample at time $t_n$ based on the light received from the optical switch at 412. For example, as described above in connection with FIG. 2A, at 414, process 400 can control an image sensor (e.g., a linear CCD or linear CMOS sensor) to capture data indicative of depths at which light was reflected by the sample based on interference between light in the sample arm and light in the second reference arm. In some embodiments, process 400 can return to 408 to switch back to the first channel and acquire data, at 410, corresponding to time $t_{n+1}$.

Figure 5:
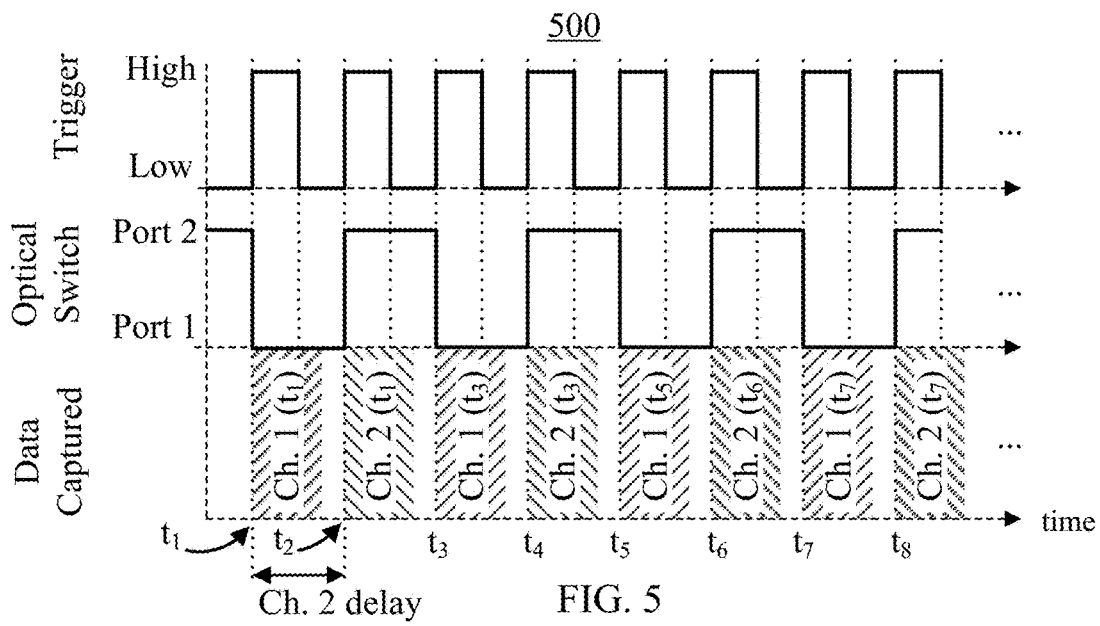
FIG. 5 shows an example of a timing diagram representing collection of image data in accordance with some embodiments of the disclosed subject matter.

FIG. 5 shows an example 500 of a timing diagram representing collection of image data in accordance with some embodiments of the disclosed subject matter. As shown in FIG. 5, a trigger signal that is used to operate the linear sensor of the spectrometer can have a first frequency. In the example shown in FIG. 5, the linear sensor is configured to capture data in response to detecting the rising edge of the trigger signal. An optical switch control signal can have a frequency that is half of the frequency of the trigger signal to control the optical switch to outputs light from channel 1 and channel 2 during consecutive data acquisitions by the linear sensor. Note that, in some cases, the acquisition time of the sensor may occupy a significant portion of the period of the trigger signal. For example, as shown in FIG. 5, if readout is triggered by the rising edge, the acquisition by the sensor may not be completed until after the corresponding falling edge of the trigger signal.

Figure 6:
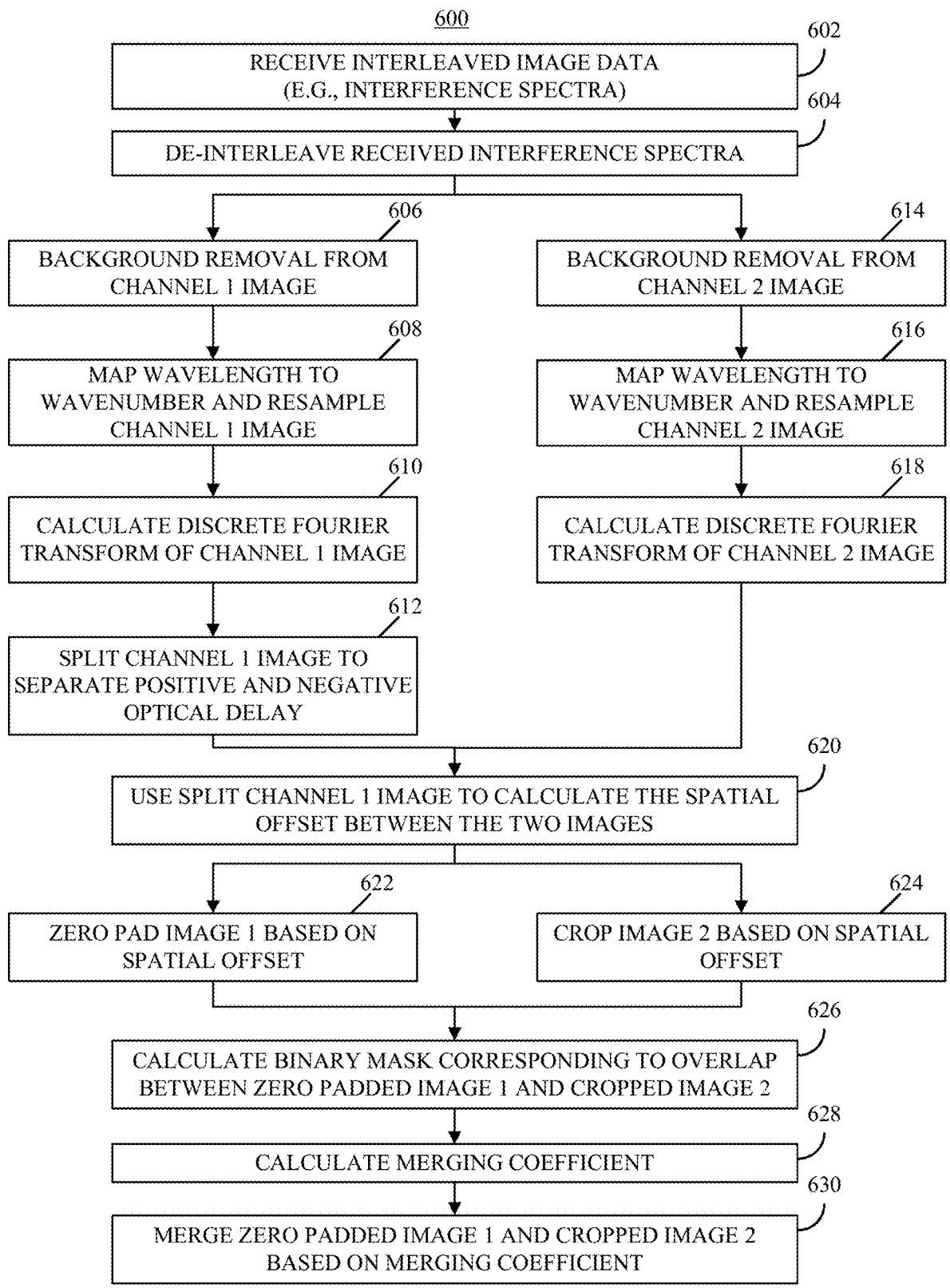
FIG. 6 shows an example of a process for synthesizing image data generated using different reference arms in accordance with some embodiments of the disclosed subject matter.

FIG. 6 shows an example 600 of a process for synthesizing image data generated using different reference arms in accordance with some embodiments of the disclosed subject matter. At 602, process 600 can receive interleaved image data corresponding to data received sequentially from channel 1 and channel 2 of an imaging system. In some embodiments, each row or column of the interleaved image data can correspond to an A scan of a sample, and pairs of consecutive columns can correspond to A scans of the same lateral location captured simultaneously. As described above in connection with FIG. 2A, in some embodiments, one of the channels can be associated with a delay such that consecutive spectra represent the state of the sample during the same time window, but having different sensitivities at different depths (e.g., the delayed reference arm can be longer, which can facilitate improved sensitivity for larger depth values). In some embodiments, the interleaved image data can be formatted in the wavelength domain, in which each column or row corresponds to a depth value. Alternatively, in some embodiments, the interleaved image data can be received in another format, such as in the wavenumber domain.

In some embodiments, the interleaved image data can be described as a data matrix representing M interference spectra, where each of the M interface spectra is associated with N samples (e.g., representing uniform intervals of spectrum corresponding to a range of depth). For example, the interleaved image data can be represented as $I(\lambda, t)_{M \times N}$.

At 604, process 600 can separate the odd and even rows (or columns) to generate separate data matrices corresponding to information received via channel 1 and channel 2, respectively. For example, the matrix $I(\lambda, t)_{M \times N}$ can be separated into two matrices $I_{Ch1}(\lambda, t)_{M/2 \times N}$ and $I_{Ch2}(\lambda, t)_{M/2 \times N}$, each representing an image of the sample corresponding to a different reference signal.

At 606, process 600 can remove a background component from the channel 1 image by calculating the average (i.e., mean) value of each value in the matrix $I_{Ch1}(\lambda, t)_{M/2 \times N}$, and uniformly subtracting the mean from the data. For example, process 600 can generate an adjusted matrix $I'_{Ch1}(\lambda, t)_{M/2 \times N}$ that corresponds to $I_{Ch1}(\lambda, t)_{M/2 \times N}$ with a background component removed, which can be represented as $I'_{Ch1}(\lambda, t)_{M/2 \times N} = I_{Ch1}(\lambda, t)_{M/2 \times N} - \text{rep}\{\text{mean}I_{Ch1}(\lambda, t)_{1 \times N}\}_{M/2 \times N}$, where $\text{mean}I_{Ch1}(\lambda, t)_{1 \times N}$ is a column vector of dimension N where each element is the mean value of all elements in the row of matrix $I_{Ch1}(\lambda, t)_{M/2 \times N}$, and rep{ } transforms the mean vector $(\text{mean}I_{Ch1}(\lambda, t)_{1 \times N})$ to a matrix of repeated similar mean vector columns.

As 608, process 600 can map the wavelengths represented in the adjusted matrix $I'_{Ch1}(\lambda, t)_{M/2 \times N}$ to the wavenumber domain (sometimes referred to as the k-domain). For example, the center wavelength $\lambda_N$ corresponding to each column can be mapped to a wavenumber $k_N$ (note that in general wavenumber corresponds to the inverse of frequency, i.e., $$k_N = \frac{1}{\lambda_N}).$$

The mapping can be represented as $I'_{Ch1}(\lambda, t)_{M/2 \times N} \rightarrow I_{Ch1}(k, t)_{M/2 \times N}$. In some embodiments, the mapping function can be calibrated for the spectrometer with linear interpolation.

At 610, process 600 can calculate a discrete Fourier transform (DFT) of the k-domain data matrix corresponding to channel 1 to generate a representation of the channel 1 image in the spatial domain. For example, process 600 can perform a discrete Fourier transform of the k-domain data matrix to generate a spatial domain data matrix $I_{Ch1}(z, t)_{M/2 \times N}$ representing the sample at various depth values $z_N$. In a more particular example, process 600 can perform a fast Fourier transform of the k-domain data matrix, which can be represented as $FFT\{I_{Ch1}(k, t)_{M/2 \times N}\} \rightarrow I_{Ch1}(z, t)_{M/2 \times N}$.

At 612, process 600 can split the channel 1 image (e.g., the spatial-domain data matrix) to separate mirror images in the channel 1 image due to ambiguity between the positive and negative delay. For example, process 600 can subdivide the channel 1 image by using the first N/2 columns (or rows) to represent one version of the mirror image, and using the next N/2 columns (or rows) to represent another version of the mirror image. In a more particular example, process 600 can generate a data matrices $I'_{Ch1}(z, t)_{M/2 \times N/2}$ and $I_{Ch1}(z, t)_{M/2 \times N/2}$, where data matrix $I'_{Ch1}(z, t)_{M/2 \times N/2}$ is based on the 1st to $(N/2)^{th}$ columns of $I_{Ch1}(z, t)_{M/2 \times N}$ and data matrix $I_{Ch1}(z, t)_{M/2 \times N/2}$ is based on the $(N/2+1)^{th}$ to Nth column of $I_{Ch1}(z, t)_{M/2 \times N}$. Note that, in some embodiments, process 600 can omit generation of one of the mirror images when only one of the mirror images is used in later processing.

At 614, process 600 can remove a background component from the channel 2 image by calculating the average (i.e., mean) value of each value in the matrix $I_{Ch2}(\lambda, t)_{M/2 \times N}$, and uniformly subtracting the mean from the data. For example, process 600 can generate an adjusted matrix $I_{Ch2}(\lambda, t)_{M/2 \times N}$ that corresponds to $I_{Ch2}(\lambda, t)_{M/2 \times N}$ with a background component removed, which can be represented as $I_{Ch2}(\lambda, t)_{M/2 \times N} = I_{Ch2}(\lambda, t)_{M/2 \times N} - \text{rep}\{I_{Ch1}(\lambda, t)_{1 \times N}\}_{M/2 \times N}$, where $\text{mean}I_{Ch2}(\lambda, t)_{1 \times N}$ is a column vector of dimension N where each element is the mean value of all elements in the row of matrix $I_{Ch2}(\lambda, t)_{M/2 \times N}$, and rep{ } transforms the mean vector $(\text{mean}I_{Ch2}(\lambda, t)_{1 \times N})$ to a matrix of repeated similar mean vector columns.

As 616, process 600 can map the wavelengths represented in the adjusted matrix $I_{Ch2}(\lambda, t)_{M/2 \times N}$ to the wavenumber domain (sometimes referred to as the k-domain). For example, the center wavelength $\lambda_N$ corresponding to each column can be mapped to a wavenumber $k_N$ (note that in general wavenumber corresponds to the inverse of frequency, i.e., $$k_N = \frac{1}{\lambda_N}).$$

The mapping can be represented as $I'_{Ch2}(\lambda, t)_{M/2 \times N} \rightarrow I_{Ch2}(k, t)_{M/2 \times N}$. In some embodiments, the mapping function can be calibrated for the spectrometer with linear interpolation.

At 618, process 600 can calculate a discrete Fourier transform (DFT) of the k-domain data matrix corresponding to channel 2 to generate a representation of the channel 2 image in the spatial domain. For example, process 600 can perform a discrete Fourier transform to the k-domain data matrix to generate a spatial domain data matrix $I_{Ch2}(z, t)_{M/2 \times N}$ representing the sample at various depth values $z_N$. In a more particular example, process 600 can perform a fast Fourier transform of the k-domain data matrix, which can be represented as $FFT\{I_{Ch2}(k, t)_{M/2 \times N}\} \rightarrow I_{Ch2}(z, t)_{M/2 \times N}$.

At 620, process 600 can use one of the split images generated at 612 and the image generated at 618 to determine a depth offset $z_{shift}$ between the two channels, which corresponds to the difference in path length between the two reference arms. In some embodiments, process 600 can use any suitable technique or combination of techniques to determine the $z_{shift}$ between the two channels. For example, process 600 can use a cross-correlation function to determine which columns in the mirror image from channel 1 correspond to columns in the image from channel 2. In some embodiments, the spatial offset can be calculated once, as the offset generally remains fixed. However, in some embodiments, the offset can be recalculated if the path length of one of the reference arms changes, and/or after a predetermined period of time and/or after a predetermined number of images have been captured (e.g., as the path length may drift over time due to environmental factors, such as temperature, etc.).

At 622, process 600 can zero pad the mirror image extracted at 612 based on the spatial offset $z_{shift}$ calculated at 620. This can cause the depth of the image extracted at 612 to substantially match the maximum depth of the image generated from channel 2. In some embodiments, the zero padding can be represented as $I_{Ch1}(z, t)_{M/2 \times N/2} \rightarrow I_{Ch1}(z, t)_{M/2 \times N'}$ to match the dimension of an image $I_{Ch2}(z, t)_{M/2 \times N'}$ generated from the channel 2 image based on the offset (e.g., as described below in connection with 624).

At 624, process 600 can crop the image generated at 618 based on the spatial offset to remove a portion of the mirror image that is not represented in the image from channel 1. For example, process 600 can generate an image $I_{Ch2}(z, t)_{M/2 \times N'} = I_{Ch2}(z, t)_{M/2 \times (N-z_{shift})}$.

At 626, process 600 can generate a mask B that represents a binarized portion $I'_{Ch2}(k, t)_{M/2 \times N/2}$ of the cropped image generated at 624, which corresponds to a portion that overlaps with the zero padded image from channel 1 generated at 622. In some embodiments, mask B can be generated based on a comparison of the mirror image of channel 1 with the main (e.g., positive delay) image from channel 2. For example, the value of each element in the mirror image of channel 1 can be compared with a threshold value. If the element has a value above the threshold a 0 can be included in the binary mask B at that position, and if the element has a value below (or equal to) the threshold a 1 can be included in the binary mask B at that position. In a more particular example, the threshold can be based on the noise value (e.g., mean and standard deviation) from a signal free region. For example, in 706, portions of the matrix within zero delay and imaging probe surface that has no reflected signal can be used to determine the threshold.

At 628, process 600 can calculate merging coefficients that can be used to merge overlapping data from the data matrices representing channel 1 and channel 2. In some embodiments, process 600 can calculate a weighted merge coefficient matrix W=Cm*B, where Cm is a merge coefficient. For example, Cm can be a coefficient that can be represented as Cm=(tanh(x)+1)/2, where x varies from $-2\pi$ to $2\pi$, and can be used to generate a vector of values for multiplication with mask B. Note that this is merely an example, and other functions, such as a linearly varying function, a step function, etc., can be used to generate the weighting coefficients.

At 630, process 600 can generate a merged image $I_m(z, x)_{M/2 \times N'}$ using the zero padded mirror image generated at 622 (corresponding to channel 1) and the cropped image generated at 624 using the merging coefficients (e.g., based on matrix W). In some embodiments, process 600 can use any suitable technique or combination of techniques to merge the images from channel 1 and channel 2. For example, $I_m(z, x)_{M/2 \times N'}$ can be generated using the following formula to generate the portion that is represented in both channel 1 and channel 2 images:

$$I_m(z,x)_{M/2 \times (N-z_{shift})} = (1-W) * I_{Ch1}(z,t)_{M/2 \times (N-z_{shift})} + W * I_{Ch2}(z,t)_{M/2 \times (N-z_{shift})}$$

In some embodiments, after generating a merged image, process 600 can cause the image to be stored (e.g., in memory, in a cache, in long term storage, etc.) and/or presented (e.g., using a display).

Figure 7A:
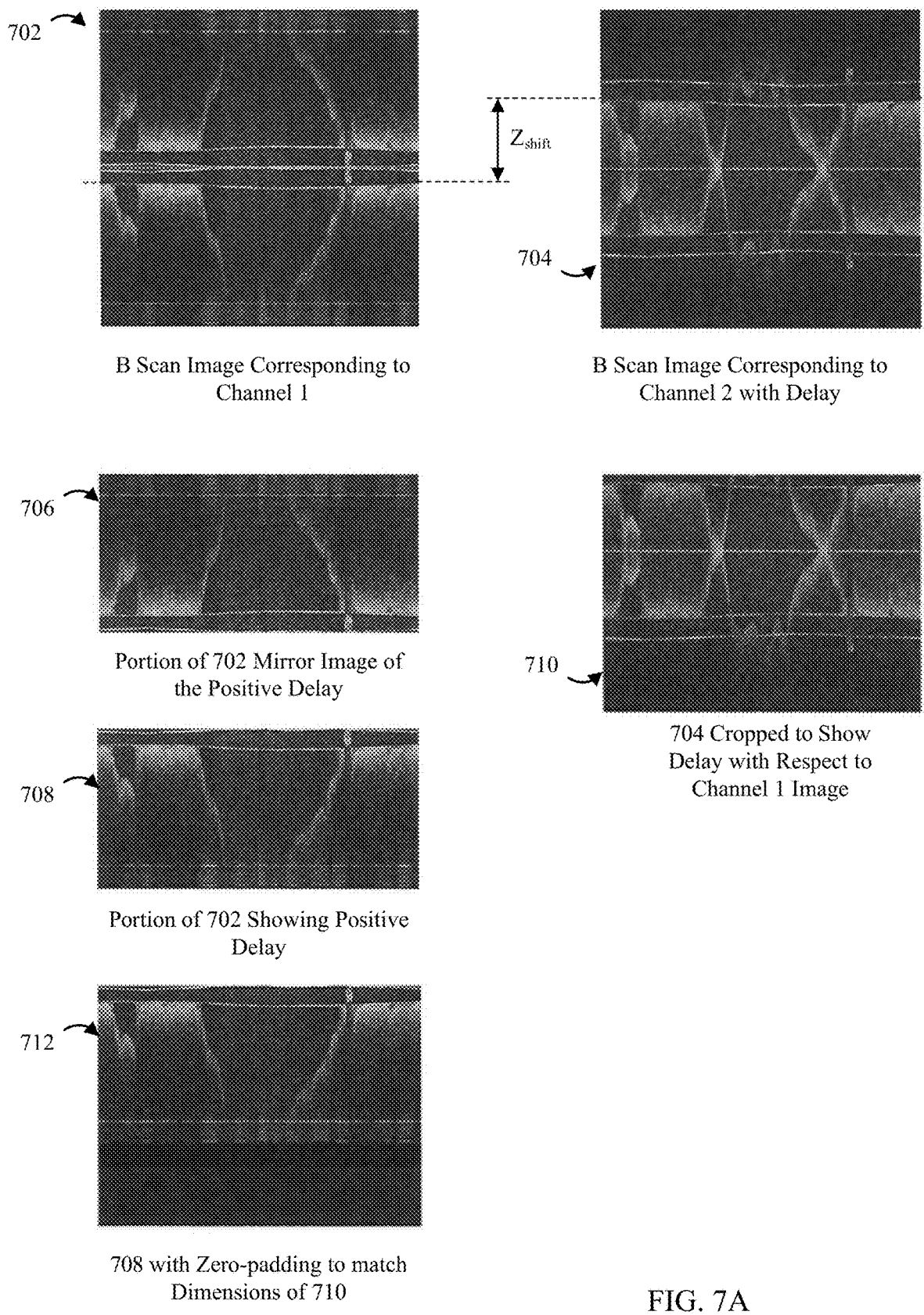
FIG. 7A shows examples of images representing various operations that can be performed during synthesis of image data generated using different reference arms in accordance with some embodiments of the disclosed subject matter.

FIG. 7A shows examples of images representing various operations that can be performed during synthesis of image data generated using different reference arms in accordance with some embodiments of the disclosed subject matter. As shown in FIG. 7A, image 702 represents odd columns (or rows) of the 2D data matrix output by the spectrometer, while image 704 represents even columns (or rows) of the 2D data matrix output by the spectrometer, resulting in images corresponding to channel 1 and channel 2 after background subtraction. Note that this is merely an example, and channel 2 can correspond to the even columns (or rows). The spatial difference between the channel 1 and channel 2 images can be observed by visually comparing images 702 and 704.

In FIG. 7A, image 706 represents a mirror image of the tissue (e.g., rather than a real image of the tissue), which can be determined because the zero delay is set just outside the imaging probe wall, and consequently, the negative delay space is occupied by mostly empty space (i.e., there should minimal reflections from the negative delay side of the zero delay). By contrast, in FIG. 7A, image 708 represents an image of the tissue, which can be determined because the zero delay is set just outside the imaging probe wall, and consequently, the positive delay space is disambiguated from the negative delay space.

Image 710 is a cropped version of image 704, which can be used to remove a portion of image 710 that overlaps with image 706, while image 712 is a version of image 708 with a number of (blank) lines corresponding to the spatial shift added to the bottom of the image.

Figure 7B:
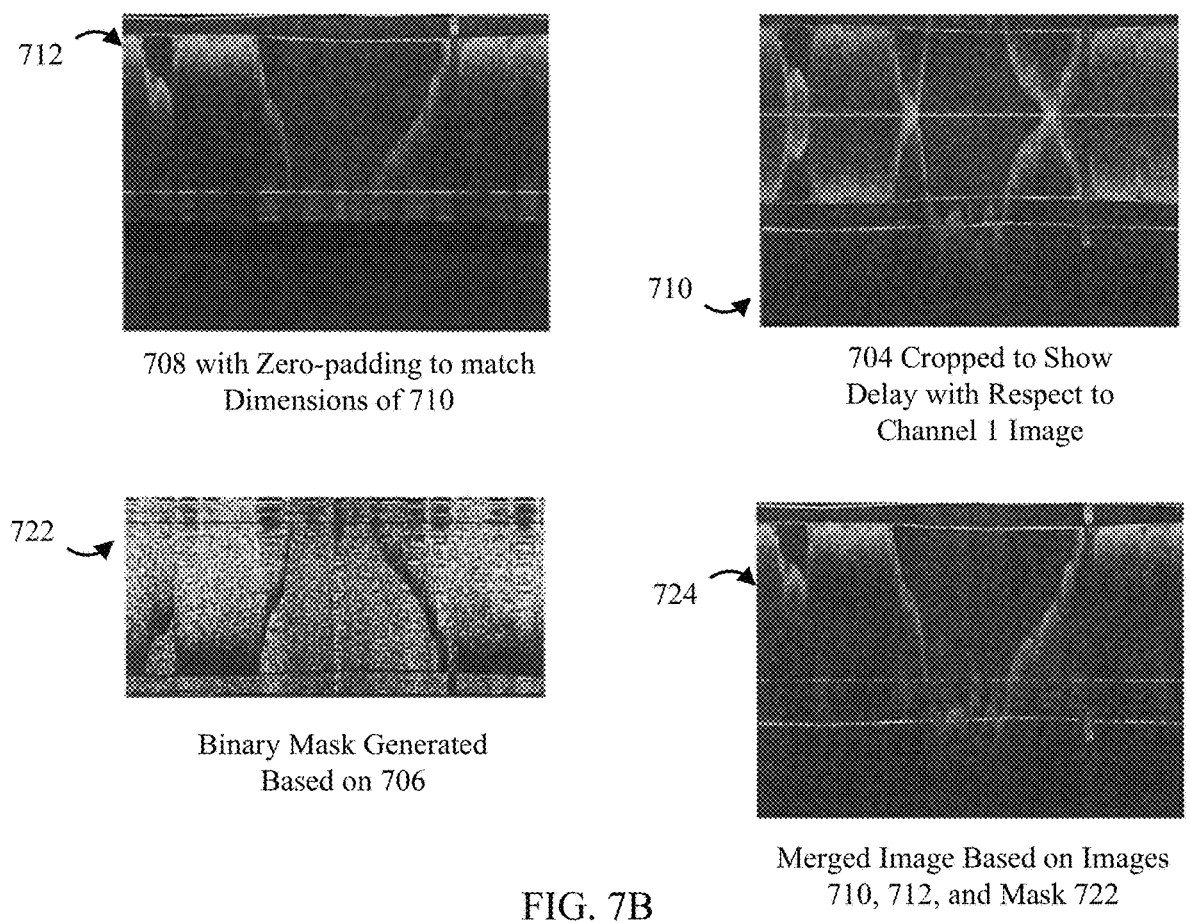
FIG. 7B shows additional examples of images representing various operations that can be performed during synthesis of image data generated using different reference arms in accordance with some embodiments of the disclosed subject matter.

FIG. 7B shows additional examples of images representing various operations that can be performed during synthesis of image data generated using different reference arms in accordance with some embodiments of the disclosed subject matter. Images 712 and 710 are reproduced in FIG. 7B for reference. As shown in FIG. 7B, a binary mask can be generated for the portion of image 710 that overlaps with zero padded image 712 based on the mirror image of the tissue in image 706.

As shown in FIG. 7B, a merged image 724 that was generated by combining images 710 and 712 using binary mask 722 and weighting coefficients Cm has greater sensitivity than the channel 1 image alone (which corresponds to an image that can be generated using conventional SD-OCT techniques), without mirror artifacts that would otherwise be present if the zero optical delay were set within the sample.

Figure 7C:
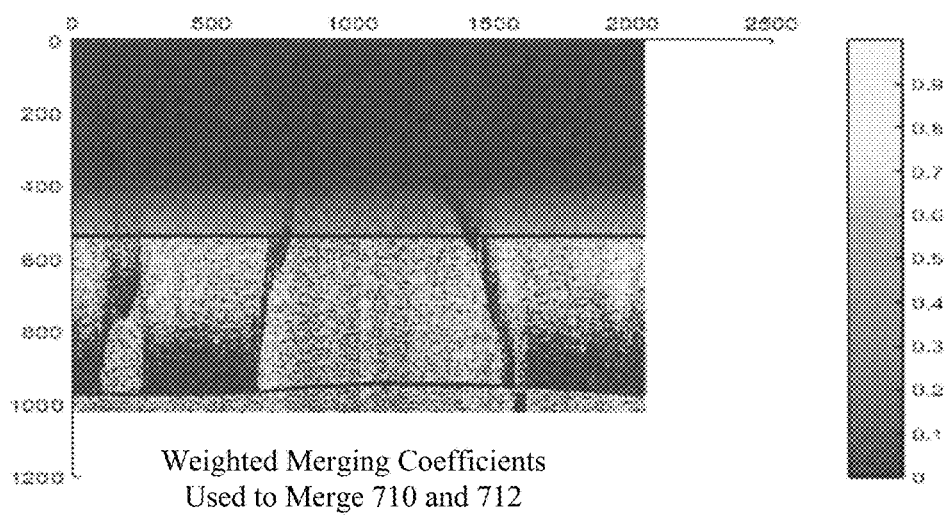
FIG. 7C shows an example of weighted merging coefficients that can be used to synthesize image data generated using different reference arms in accordance with some embodiments of the disclosed subject matter.

FIG. 7C shows an example of weighted merging coefficients that can be used to synthesize image data generated using different reference arms in accordance with some embodiments of the disclosed subject matter.

Figure 8:
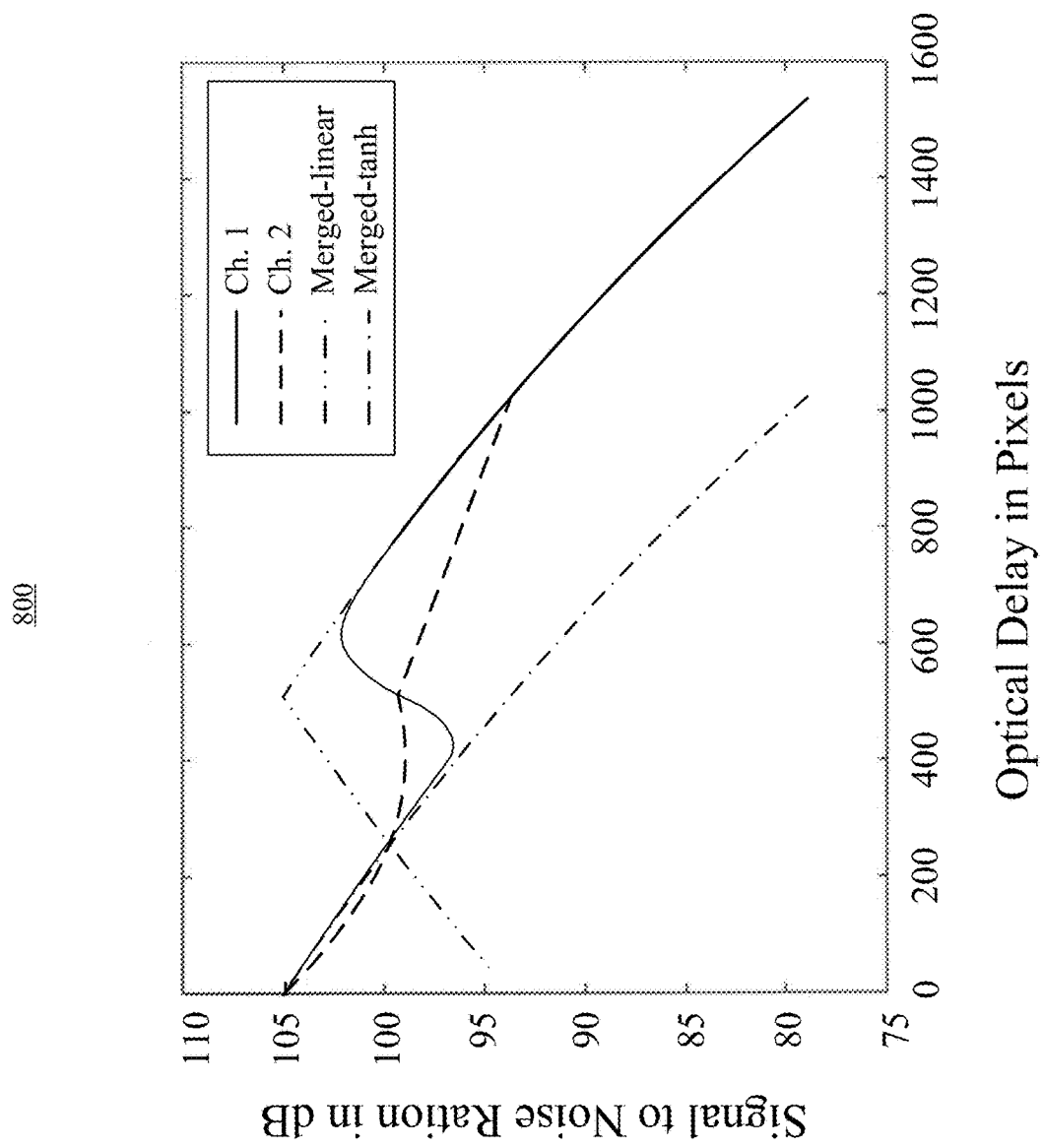
FIG. 8 shows examples of sensitivity roll-off observed for a first reference arm, a second reference, and a combination of the first and second reference arms of a spectral domain optical coherence tomography system implemented in accordance with some embodiments of the disclosed subject matter.

FIG. 8 shows examples of sensitivity roll-off observed for a first reference arm, a second reference, and a combination of the first and second reference arms of a spectral domain optical coherence tomography system implemented in accordance with some embodiments of the disclosed subject matter. As shown in FIG. 8, measured maximum sensitivities of an example system corresponding to each of the two reference delays were about ~105 dB. More particularly, FIG. 8 shows depth-dependent sensitivity for the two reference arms individually (Ch. 1 and Ch. 2 curves) and for the combined data (Merged-linear and Merged-tanh, respectively). The latter two curves show the resultant sensitivity roll-off when linear and (tanh+1)/2 functions, respectively, were used to generate merging coefficients. As shown, the sensitivity for the first arm was ~105 dB near the zero-delay line, but decayed by about 20 dB at the end of the imaging depth range (i.e. ~6 mm from the zero optical delay for the example system described below). The delay of the other reference arm was set to be about half of the maximum imaging depth range (i.e. ~3 mm away from the zero-delay line for the example system described below), which resulted in a sensitivity of ~98 dB at the ~6 mm scan with a peak sensitivity of ~105 dB at ~3 mm. The offset between the two reference arms was chosen such that for an imaging depth of 0-3 mm, reference 1 provided better sensitivity (105 dB to 98 dB) and for 3-6 mm, reference 2 provided better sensitivity (105 dB to 98 dB). Accordingly, in some embodiments, the mechanisms described herein can be used to generate SD-OCT images with a sensitivity that remains between the 105 dB to 98 dB throughout the imaging depth range. This can generate a>10 dB improvement in sensitivity compared to conventional SD-OCT systems where sensitivity decays from 105 dB to 85 dB (e.g., as shown for Ch. 1 in FIG. 8).

An example system based on example 200 was built to generate example sensitivities. The example system incorporated a 3 milliwatt (mW) superluminescent diode (SLD) with a 3 dB bandwidth of ~100 nanometers (nm), centered at about 1310 nm. A booster optical amplifier (BOA, 87 nm FWHM) was used to amplify light from the SLD. A polarization controller was used between the SLD and BOA to optimize light amplification and its spectral profile, as the light amplification by the BOA that was used was polarization sensitive. A 75/25 fiber splitter was used to divide the light from the BOA into sample and reference arms. In the sample arm, an optical circulator was used to direct light toward the sample, and to collect back-reflected light from the sample. The back-reflected light from the sample was split using a 50/50 fiber splitter to direct half of the back-reflected light toward a first reference arm, and the other half toward a second reference arm. Another 50/50 fiber splitter was used to split the reference arm light, with one reference arm length set such that it was at the zero-delay point with respect to the sample arm (i.e., to have an identical optical path length to the sample arm). A linear translation stage and collimation assembly was used to set the path length of the second reference arm to have a predetermined, 3 mm optical path length offset compared to the first reference arm, which was about half the ranging depth offered by a 2048-pixel line scan camera used in a spectrometer used in the example system.

Fiber couplers with a splitting ratio of 99/1 were used to combine light returning from the evenly split sample and reference arms. The 99% outputs from these couplers were passed to the spectrometer through a 2×1 optical switch, with one of the 99/1 coupler outputs connected directly to input port 1 of the optical switch, and the other 99/1 coupler output transmitted through a ~1.5 km fiber delay line (FDL) prior to being connected to input port 2 of the optical switch. An output port of the optical switch was connected to the spectrometer (a Cobra super SWIR 1310, Wasatch Photonics). The ~1.5 km length of the FDL was selected such that a temporal delay was induced that was equivalent to the acquisition time of a single line of data by the 140 kHz line scan camera (7.14 microseconds (µs)) (GL2048 R, Sensors Unlimited) used with the spectrometer. Based on the input signal to the optical switch, it blocked light returning from channel-2 (Ch-2) while it passed light from channel-1 (Ch-1) and vice versa (e.g., as described above in connection with FIG. 2A). The isolation efficiency of the optical switch was ~20 dB, which could potentially lead to cross-talk interference being detected in the OCT images. However, the FDL eliminated the detection of cross-talk interference, as it made the optical path length in one channel significantly longer than that of the ranging depth of the system. Two synchronized TTL signals at 140 kHz and 70 kHz were used to trigger the detection of linear array data (2048 pixels per line scan) and to drive the optical switch. This configuration allowed alternate interferometric spectra to be acquired by the camera resulting from interference between the sample (within the same temporal window) and the two different reference arms. Spectra associated with interference between the sample and each reference arm were digitized sequentially and processed individually (e.g., as described above in connection with FIGS. 6 and 7). The processing steps included background subtraction, resampling, fast Fourier transformation, and algorithmic mixing of the A-lines to generate a single OCT image with a decreased sensitivity roll-off.

A final, mixed image was generated by merging image-1 (image corresponding to Ref-1 and Ch-1) with image-2 (image corresponding to Ref-2 and Ch-2). However, due to positive vs. negative distance ambiguity resulting from the Fourier transform of real data, the tissue present within 3 mm of the imaging probe's surface could lead to mirror-image artifacts in image-2. Mirror artifacts were mitigated in the combined image, by removes mirror artifacts while merging the two images to generate final image having enhanced sensitivity for deeper portions of the ranging depth and increase the imaging range of the system than that of standard SDOCT system.

Excised swine colon tissue was used to demonstrate the capacity of the mechanisms described herein to acquire high quality image data at depth. An 11-mm diameter tethered OCT capsule was used as a scanning probe for generating the image data. The imaging capsule probe was placed in the lumen of the intact swine colon, and circumferential images of the intestinal wall were acquired. Images with single and dual reference arms were acquired for comparison.

Images 702 and 704 depict the OCT images taken by the capsule probe from excised swine colon tissue following Ch1 and Ch2. Images 706 and 708 are the images split from image 702, to separate real and mirror images. Image 722 is a binary mask obtained from image 706, with the binary mask being used to remove the overlapped mirror artifact from image 704. The optical delay offset between the images 702 and 704 was computed using a cross-correlation scheme. Image 710 depicts a cropped version of image 704 that shows only the positive optical delay with respect to the Ch1 image 702. Image 712 shows a zero-padded version of image 708 to match the dimensions of FIG. 710 before merging. FIG. 7C shows weighted merging coefficients calculated from binary mask 722 and the merging function (in this case the merging function as (tanh+1)/2 was used to gradually change the weight for merging coefficient from image 1 to image 2). Image 724 shows a final merged image. As shown in FIGS. 7A and 7B, the OCT image intensity in image 702 generated using only data from Ch-1 was stronger for tissue close to the imaging capsule probe's surface, whereas the OCT image intensity from tissue further from the capsule's surface is lower due to sensitivity roll-off. As can be expected, the deeper region in image 702 shows very dull image intensity. By contrast, image 704 shows better signal strength for tissues located longer distance from the surface of the tissue due to the additional delay in Ch2. These characteristics were combined using the mechanisms described herein to generate merged image 724, which shows relatively strong sensitivity throughout, facilitating improved visualization of the lumen wall at all depths within the maximum depth of the SD-OCT system. The improvement afforded by the dual reference SD-OCT system can also be clearly seen by comparing scan converted single- and dual-reference images (e.g., images 308 and 310).

Figure 9:
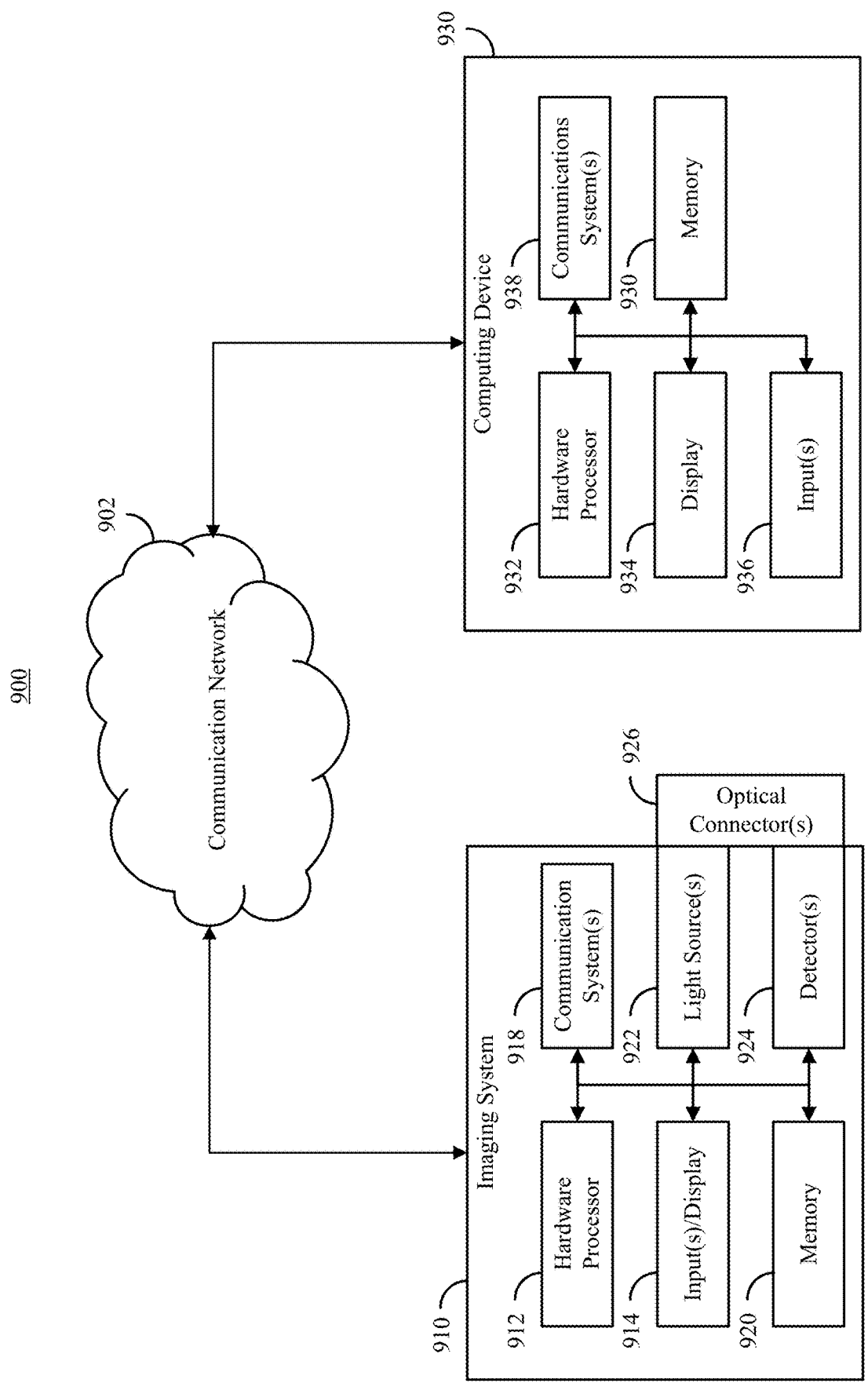
FIG. 9 shows an example of hardware that can be used to implement an imaging device and/or a computing device that can be used in connection with some embodiments of mechanisms for multiple reference arm spectral domain optical coherence tomography implemented in accordance with some embodiments of the disclosed subject matter.

FIG. 9 shows an example 900 of hardware that can be used to implement an imaging device and/or a computing device that can be used in connection with some embodiments of mechanisms for multiple reference arm spectral domain optical coherence tomography implemented in accordance with some embodiments of the disclosed subject matter. For example, hardware shown in FIG. 9 can be used to implement at least a portion of spectrometer 124. As shown in FIG. 9, in some embodiments, an imaging system 910 can include a hardware processor 912, a user interface and/or display 914, one or more communication systems 918, memory 920, one or more light sources 922, one or more electromagnetic detectors 926, and/or one or more optical connectors 926. In some embodiments, hardware processor 912 can be any suitable hardware processor or combination of processors, such as a central processing unit (CPU), a graphics processing unit (GPU), a microcontroller (MCU), a field programmable gate array (FPGA), a dedicated image processor, etc. In some embodiments, input(s) and/or display 914 can include any suitable display device(s), such as a computer monitor, a touchscreen, a television, a transparent or semitransparent display, a head mounted display, etc., and/or input devices and/or sensors that can be used to receive user input, such as a keyboard, a mouse, a touchscreen, a microphone, a gaze tracking system, motion sensors, etc.

In some embodiments, communications systems 918 can include any suitable hardware, firmware, and/or software for communicating information over a communication network 902 and/or any other suitable communication networks. For example, communications systems 918 can include one or more transceivers, one or more communication chips and/or chip sets, etc. In a more particular example, communications systems 918 can include hardware, firmware and/or software that can be used to establish a Wi-Fi connection, a Bluetooth connection, a cellular connection, an Ethernet connection, an optical connection, etc.

In some embodiments, communication network 902 can be any suitable communication network or combination of communication networks. For example, communication network 902 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 902 can be a local area network, a wide area network, a public network (e.g., the Internet), a private or semi-private network (e.g., a corporate or university intranet), any other suitable type of network, or any suitable combination of networks. Communications links shown in FIG. 9 can each be any suitable communications link or combination of communications links, such as wired links, fiber optic links, Wi-Fi links, Bluetooth links, cellular links, etc.

In some embodiments, memory 920 can include any suitable storage device or devices that can be used to store instructions, values, etc., that can be used, for example, by hardware processor 912 to process image data generated by one or more optical detectors, to present content using input(s)/display 914, to communicate with a computing device 930 via communications system(s) 918, etc. Memory 920 can include any suitable volatile memory, non-volatile memory, storage, any other suitable type of storage medium, or any suitable combination thereof. For example, memory 920 can include RAM, ROM, EEPROM, one or more flash drives, one or more hard disks, one or more solid state drives, one or more optical drives, etc. In some embodiments, memory 920 can have encoded thereon a computer program for controlling operation of imaging system 910. In some such embodiments, hardware processor 912 can execute at least a portion of the computer program to control one or more light sources and/or detectors (e.g., to capture OCT data as described above in connection with FIG. 4), to generate images and/or calculate values (e.g., an OCT image, etc.), transmit and/or receive information to/from computing device 930, combine OCT images from different channels to generate merged OCT images with improved sensitivity roll-off (e.g., as described above in connection with FIG. 6), etc.

In some embodiments, imaging system 910 can include one or more light sources 922, such a coherent or incoherent light source (e.g., a light emitting diode or combination of light emitting diodes, a white light source, etc.), which can be a broadband light source, or a narrower band light source. For example, the bandwidth of the light source can be selected to provide a range of wavelengths that facilitates depth detection over a maximum imaging range of the SD-OCT system. Additionally, in some embodiments, light sources 922 can be associated with one or more filters.

In some embodiments, imaging system 910 can include one or more light detectors 924, such as one or more photodiodes, and/or one or more image sensors (e.g., a CCD image sensor or a CMOS image sensor, either of which may be a linear array or a two-dimensional array). For example, in some embodiments, detectors 924 can include one or more detectors configured to detect light at specific wavelengths (e.g., using filters, using optics to guide light of different wavelengths to different portions of the detector(s), etc.)

In some embodiments, imaging system 910 can include one or more optical connectors 926. For example, such optical connectors can be fiber optic connectors configured to form an optical connection between light source(s) 922 and/or detector 924 and an optical fiber (e.g., as part of a fiber optic cable).

In some embodiments, computing device 930 can include a hardware processor 932, a display 934, one or more inputs 936, one or more communication systems 938, and/or memory 940. In some embodiments, hardware processor 932 can be any suitable hardware processor or combination of processors, such as a CPU, a GPU, an MCU, an FPGA, a dedicated image processor, etc. In some embodiments, display 934 can include any suitable display devices, such as a computer monitor, a touchscreen, a television, a transparent or semitransparent display, a head mounted display, etc. In some embodiments, inputs 936 can include any suitable input devices and/or sensors that can be used to receive user input, such as a keyboard, a mouse, a touchscreen, a microphone, a gaze tracking system, motion sensors, etc.

In some embodiments, communications systems 938 can include any suitable hardware, firmware, and/or software for communicating information over communication network 902 and/or any other suitable communication networks. For example, communications systems 938 can include one or more transceivers, one or more communication chips and/or chip sets, etc. In a more particular example, communications systems 938 can include hardware, firmware and/or software that can be used to establish a Wi-Fi connection, a Bluetooth connection, a cellular connection, an Ethernet connection, etc.

In some embodiments, memory 940 can include any suitable storage device or devices that can be used to store instructions, values, etc., that can be used, for example, by hardware processor 932 to present content using display 934, to communication with one or more imaging devices, etc. Memory 940 can include any suitable volatile memory, non-volatile memory, storage, any other suitable type of storage medium, or any suitable combination thereof. For example, memory 940 can include RAM, ROM, EEPROM, one or more flash drives, one or more hard disks, one or more solid state drives, one or more optical drives, etc. In some embodiments, memory 940 can have encoded thereon a computer program for controlling operation of computing device 930. In such embodiments, hardware processor 932 can execute at least a portion of the computer program to receive content (e.g., image content) from one or more imaging devices (e.g., imaging device 910), combine OCT images from different channels to generate merged OCT images with improved sensitivity roll-off (e.g., as described above in connection with FIG. 6), present content (e.g., images and/or values,) transmit content to one or more other computing devices and/or imaging systems, etc.

In some embodiments, computing device 930 can be any suitable computing device, such as a general purpose computer or special purpose computer. For example, in some embodiments, computing device 930 can be a smartphone, a wearable computer, a tablet computer, a laptop computer, a personal computer, a server, etc. As another example, in some embodiments, computing device 930 can be a medical device, a system controller, etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/ or any suitable intangible media.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. A method for spectral domain optical coherence tomography, the method comprising:
   receiving, by a processor, a matrix of data comprising:
   a first vector of data generated using a first reference arm having a first path length and representing a state of a sample in a first time window that includes a first time,
   a second vector of data generated using a second reference arm having a second path length and representing the state of the sample in the first time window,
   a third vector of data generated using the first reference arm and representing a state of the sample in a second time window that does not include the first time, and
   a fourth vector of data generated using the second reference arm and representing the state of the sample in the second time window;
   generating, by the processor, first image data based on the first vector of data and the third vector of data;
   generating, by the processor, second image data based on the second vector of data and the fourth vector of data;
   calculating, by the processor, a spatial offset between the first image data and the second image data based on a comparison of a portion of the first image data and a portion of the second image data;
   appending, by the processor, a first plurality of vectors to the portion of the first image data to generate a zero padded image, wherein the number of vectors appended is based on the spatial offset;
   removing, by the processor, a second plurality of vectors from the second image data to generate a cropped image, wherein the number of vectors removed is based on the spatial offset; and
   merging, by the processor, the zero padded image and the cropped image to generate an image of the sample with decreased sensitivity roll-off.

2. The method of claim 1, wherein the first vector is a first row of the matrix and the second vector is a second row of the matrix.

3. The method of claim 2, wherein the first vector comprises at least N elements, each of the N elements corresponds to a pixel of the image sensor, and the matrix comprises at least N columns.

4. The method of claim 3, wherein the spatial offset corresponds to a particular number of columns of the N columns.

5. The method of claim 1, wherein each entry in the first vector corresponds to a wavelength, and wherein the method further comprises mapping the wavelength for each element to a wavenumber k.

6. The method of claim 5, further comprising performing a discrete Fourier transform to convert each element of the first vector to a depth value.

7. The method of claim 1, further comprising generating a real image of the sample based on the first image data by subdividing the matrix into two submatrices by selecting vectors on a positive side of a zero delay for inclusion in a first submatrix and selecting vectors on a negative side of the zero delay for inclusion in a second submatrix.

8. The method of claim 7, wherein the portion of the first image data corresponds to the first submatrix.

9. The method of claim 7, further comprising generating a binary mask based on a comparison of the second submatrix and a shifted submatrix that includes values generated using the second reference arm.

10. The method of claim 9, further comprising generating a weighting matrix W comprising a plurality of weighting coefficients Cm based on the binary mask and a merging function.

11. The method of claim 10, wherein the merging function is $Cm=(\tanh(x)+1)/2$, where x varies from $-2\pi$ to $2\pi$.

12. The method of claim 1, wherein the first vector and the second vector correspond to a first lateral position on a surface of the sample, and the third vector and fourth vector correspond to a second lateral position on the surface of the sample.

* * * * *

UNITED STATES PATENT AND TRADEMARK OFFICE
CERTIFICATE OF CORRECTION

PATENT NO. : 11,713,961 B2
APPLICATION NO. : 17/473308
DATED : August 1, 2023
INVENTOR(S) : Guillermo J. Tearney et al.

It is certified that error appears in the above-identified patent and that said Letters Patent is hereby corrected as shown below:

In the Specification

Column 16, Line 12, "$I_{CH2}(\lambda,t)_{M/2 \times N}$" should be -- $I'_{CH2}(\lambda,t)_{M/2 \times N}$ --.

Column 16, Line 14, "$I_{CH2}$" should be -- $I'_{CH2}$ --.

Column 16, Line 22, "$I_{CH2}(\lambda,t)_{M/2 \times N}$" should be -- $I'_{CH2}(\lambda,t)_{M/2 \times N}$ --.

Column 17, Line 4, "$t)_{M/2 \times N'''}$" should be -- $t)_{M/2 \times N'}$ --.

Column 17, Line 5, "$I_{CH2}(z,t)_{M/2 \times N'''}$" should be -- $I_{CH2}(z,t)_{M/2 \times N'}$ --.

Signed and Sealed this
Twenty-sixth Day of December, 2023

Katherine Kelly Vidal
*Director of the United States Patent and Trademark Office*